United States Patent
Seipel

(10) Patent No.: US 11,110,141 B2
(45) Date of Patent: *Sep. 7, 2021

(54) HERBAL COMPOSITIONS FOR THE PREVENTION OR TREATMENT OF URINARY INCONTINENCE AND OVERACTIVE BLADDER

(71) Applicant: Tracey Anne Seipel, Kelvin Grove (AU)

(72) Inventor: Tracey Anne Seipel, Kelvin Grove (AU)

(73) Assignee: Rox IP Pty Ltd.

( * ) Notice: Subject to any disclaimer, the term of this patent is extended or adjusted under 35 U.S.C. 154(b) by 543 days.

This patent is subject to a terminal disclaimer.

(21) Appl. No.: 15/261,021

(22) Filed: Sep. 9, 2016

(65) Prior Publication Data

US 2016/0375075 A1    Dec. 29, 2016

Related U.S. Application Data

(63) Continuation of application No. 13/725,381, filed on Dec. 21, 2012, now Pat. No. 9,452,191.

(60) Provisional application No. 61/580,125, filed on Dec. 23, 2011.

(51) Int. Cl.
| | | |
|---|---|---|
| *A61K 36/54* | (2006.01) | |
| *A61K 36/185* | (2006.01) | |
| *A61K 36/12* | (2006.01) | |
| *A61K 36/11* | (2006.01) | |

(52) U.S. Cl.
CPC .............. *A61K 36/54* (2013.01); *A61K 36/11* (2013.01); *A61K 36/12* (2013.01); *A61K 36/185* (2013.01)

(58) Field of Classification Search
CPC ....... A61K 36/185; A61K 36/11; A61K 36/54
USPC .................. 424/725, 773, 775, 779
See application file for complete search history.

(56) References Cited

U.S. PATENT DOCUMENTS

| | | | | |
|---|---|---|---|---|
| 7,147,876 B2 * | 12/2006 | Riley | ....................... | A61K 8/67 424/744 |
| 7,378,115 B2 | 5/2008 | Seipel | | |
| 2004/0180104 A1 * | 9/2004 | Lin | ........................... | A23F 3/34 424/735 |
| 2006/0040004 A1 * | 2/2006 | Seipel | .................. | A61K 9/0014 424/762 |
| 2013/0164397 A1 | 6/2013 | Seipel | | |

OTHER PUBLICATIONS

Naturopathogy Digest, Online, UR: http://www.naturopathydigest.com/nutrition_herbs/hbers/lindera.php archived toNov. 15, 2006, using archive.org, one page.*

Siddique et al. Life Sci. 2001. vol. 88(7-8), pp. 285-293; one-page Abstract enclosed.*

Webstie dictionary definition of tannin. Downloaded on Feb. 4, 2019 from http://www.collinsdictionary.com /us/dictionary/english/tannin; five pages.*

Pengelly A, 1996. The constituents of medicinal plants; an introduction to the chemistry and therapeutics of herbal medicine. Sunflower Herbal 2nd edition, Merriwa, NSW, Australia, 1996.

Nagao A, Seki M, Kobayashi H, 1999. Inhibition of xanthine oxidase by flavonoids. Biosci Biotechnology Biochemistry; 63(10): 1787-90.

Steels E, Ryan J, Seipel T, Rao A, 2002. Crateva and Equisetum reduce urinary incontinence symptoms. Australian Continence Journal; 8 (3).

Schauss AG, Spiller G, Chaves S, Gawlicka A, 2006. Reducing the symptoms of overactive bladder and urinary incontinence: results of a two-month, double-blind, placebo-controlled clinical trial. Poster presentation FASEB, San Francisco, Apr. 2006.

Robinson D, Pearce KF, Preisser JS, Dugan E, Suggs PK and Cohen SJ, 1998. Relationship between patient reports of urinary incontinence symptoms and quality of life measures. Obstetrics and Gynaecology; 91 (2): 224-228.

Coyne K, Payne C, Bhattacharyya S, Revicki D, Thompson C, Corey R, Hunt T, 2004. The impact of urinary urgency and frequency on health-related quality of life in overactive bladder: Results from a national community survey. Value in health; 7(4).

Bone K. Clinical Applications of Ayurvedic and Chinese Herbs, 1997. Monographs for the western herbal practitioner. Phytotherapy Press, Warwick, Queensland, Australia.

Geetha T, Varalakshmi P, 2001. Anti-inflammatory activity of lupeol linoleate in rats. Journal of Ethnopharacology; 76(1): 77-80.

Geetha T, Varalakshmi P, 1999. Anticomplement activity of triterpenes from Crataeva nurvala stem bark in adjuvant arthritis in rats. General Pharmacology; 32(4): 495-7.

Chang Wang, Yue Dai, Jian Yang, Guixin Chou, Changhong Wang, Zhengtao Wang, 2007. Treatment with total alkaloids from Radix Linderae reduces inflammation and join destruction in type II collagen-induced model for rheumatoid arthritis. Journal of Ethnopharmacology; 111: 322-328.

Deshpande P.J., Sahu M, Kumar P, 1982. Crataeva nurvala Hook and Forst (Varuna) the Ayurvedic drug of choice in urinary disorders. Indian Journal of Medical Research; 76 (suppl) December; 46-53.

Anand R, Patnaik GK, Kamal Roy, Bhadur AP, 1995. Antioxaluric and anticalciuric activity of lupeol derivatives. Indian Journal of Pharmacology; 27: 265-268.

Grases F, Melero G. Costa-Bauza A, Prieto R, March JG, 1994. Urolithiasis and phytotherapy. International Journal of Urology and Nephrology; 26(5): 507-511.

(Continued)

*Primary Examiner* — Susan Hoffman
(74) *Attorney, Agent, or Firm* — Steve Hassid; Partners Law Group, Inc.

(57) ABSTRACT

Provided in one embodiment is an herbal compositions for the prevention or treatment of urogenital system disorders including urinary incontinence, overactive bladder, enuresis, benign prostatic hyperplasia, nocturia, cystitis, urinary calculi, or a urinary tract infection. Specifically one embodiment provides compositions that contain *Crateva nurvala*, *Equisetum arvense*, and *Lindera aggregata* and methods of use thereof.

12 Claims, 5 Drawing Sheets

(56) References Cited

OTHER PUBLICATIONS

Varalakshmi P, Shamila Y, Latha E. Effect of Crataeva nurvala in experimental urolithiasis. J Ethnopharmacology 1990; 28: 313-321.
Malini MM, Baskar R, Varalakshmi P, 1995. Effect of lupeol, a pentacyclic triterpene, on urinary enzymes in hyperozaluric rats. Jpn J Med Sci Biol Oct-Dec; 48(5-6): 211-20.
Yubin Luo, Mei Liu, Xiujan Yao, Yufeng Xia, Yue Dal, Guixin Chou and Zhengtao Wang, 2009. Total alkaloids from Radix Linderae prevent the production of inflammatory mediators in lipopolysaccharide-stimulated RAW 264.7 cells by suppressing NF-kB and MAPKs activation. Cytokine; 46(1): 104-110.
Qinglin L, Guixin C, Changgui D, Zhengtao W, Fang H, Dec. 1997. Studies on the analgesic and anti-inflammatory action of radix Linderae extract. Journal of Chinese Medicinal Materials. (China Pharmaceutical University, Nanjing 210038) (Abstract).
Runwei Yan, Yang Yang, Ying Ying Zeng, Guolin Zou, 2009. Cytotoxity and antibacterial activity of Lindera strychnifolia essential oils and extracts. Journal of Ethnopharmacology; 121: 451-455.
Nagaraj M, Sunitha S, Varalakshmi P, 2000. Effect of lupeol, a pentacyclic triterpene, on the lipid peroxidation and antioxidant status in rat kidney after chronic cadmium exposure. Journal of Applied Toxicology; 20(5): 413-417.
Ohno T, Takemura G, Murta I, Kagawa T, Akao S, Minatoguchi S, Fujiwara T and Fujiwara H, 2005. Water extract of the root of Lindera strychnifolia slows down the progression of diabetic nephropathy in db/db mice. Life Sciences; 77(12): 1391-1403.
Bensky D and Gamble A, 1993. Chinese Herbal Materia Medica, Revised Edition. England Press, Seattle, Washington, USA.
Shimomura M, Ushikoshi H, Hattori A, Murata I, Ohno Y, Aoyama T, Kawasaki M, Nishigaki K, Takemura G, Fujiwara T, Fujiwara H, Minatoguchi S, 2010. Treatment with Lindera strychnifolia reduces blood pressure by decreasing sympathetic nerve activity in spontaneously hypertensive rats. American Journal of Chinese Medicine; 38(3): 561-8.
Noda Y, Mori A, Anzai K, Packer L, 1999. Superoxide anion radical scavenging activity of Uyaka (Lindera strychnifolia), a natural extract used in traditional medicine. Antioxidant Food Supplements in Human Health.
Bin Li, Gil-Saeng Jeong, Dae-Gill Kang, Ho-Sub Less and Youn-Chul Kim, 2009. Cytoprotective effects of lindenenyl acetate isolated from Lindera strychnifolia on mouse hippocampal HT22 cells. European Journal of Pharmacology. Neuropharmacology and Analgesia; 16(1-3): 58-65.
Pathak AS, Aboseif SR, 2005. Overactive Bladder: Drug therapy versus nerve stimulation. Nat Clin Pract Urol, 2 (7): 310-311.
Tapp AJS, et al., The treatment of detrusor instability in post-menopausal women with oxybutynin chloride: a double blind placebo controlled study, 1990. British Journal of Obstetrics and Gynecology, 97: 521-6.
Wada Y, et al., Comparison of the effects of various anticholinergic drugs on human isolated urinary bladder, 1995. Arch. Int. Pharmacodyn. Ther., 330(1): 76-89.
Bone K, Mills S, Principles and Practice of Phytotherapy. Churchill Livingstone, 2000; 35, 220-222.
Valnet J, The Practice of Aromatherapy. Saffron Walden, The C. W. Daniel Company, Essex, England, 1980; 120-121.
Battaglia S, The Complete Guide to Aromatherapy. The Perfect Potion Pty Ltd, Virginia, Brisbane, Qld, Australia, 1995; 110-113, 116, 150-151, 158-159, 182-183, 184-185, 187.
Price S, Practical Aromatherapy: How to Use Essential Oils to Restore Vitality. Thorsons, Harper Collins Publishers, California, U.S. 1983; 157-8, 170-171, 174, 185.
Lawless J, The Encyclopedia of Essential Oils: The Complete Guide to the Use of Aromatics in Aromatherapy, Herbalism, Health & Well-Being. Element Books for Jacaranda Wiley, Ltd, Australia, 1992; 76-77, 88-89, 135-136.
Sheppard-Hanger S, The Aromatherapy Practitioner Manuel. Aquarius Publishing, Willetton, Western Australia, 1995; 183.
Sellar W, The Directory of Essential Oils. Saffron Walden, The C.W. Daniel Company, Essex, England, 1992; 50-51, 106-107.
Varalaakshmi P, et. al., Effect of Crateava Nurvala on the Biochemistry of the Small Intestinal Tract of Normal and Stone-forming rats 1991. J. Ethnopharmacology, 31: 67-73.
Tisserand, Balacs, Essential Oil Safety. A Guide for Health Care Professionals. Churchill Livingstone, U.K., 1995; 28-29, 31, 33-34.
Holmes P, The Energetics of Western Herbs: An Herbal Reference Integrating Western and Oriental Herbal Medicine Traditions. Artemis Press, Boulder, Colorado, USA, 1989; 567-569, 792.
Damian, Aromatherapy Scent and Psyche. Healing Arts Press, Rochester, Vermont, Canada, 1995; 187-188.
Price S, The Aromatherapy Workbook. Thorsons (Harper Collins), California, USA, 1993; 67.
Chidell L, Aromatherapy. A Definitive Guide to Essential Oils. Hooder and Stoughton Ltd, Kent, US, 1992; 23-24, 80-81.
Davis P, Aromatherapy An A-Z. The C. W. Daniel Company, Essex, England, 1998; 194.
Caddy R, Aromatherapy Essential Oils in Colour. Amberwood Publishing Ltd, East Horsley, Surrey, England, 1997; 14.
D'Agostino M, et al., Sterols from Equisetum arvense, 1984. Boll. Soc. ital. Biol. Sper., 30;60(12): 2241-5.
Perez Gutierrez RM, et al., Diuretic Activity of Mexican Equisetum, 1985. J. Ethnopharmacol., 14(2-3):269-272.
Nadkarni KM, et al., Indian Materia Medica. Bombay Popular Prakashan; British Herbal Pharmacopeia. British Herbal medicine Association 1983.
Salvat A, et al., 2001. Lett. Appl. Microbiology, 32(5): 293-7.
Xu and Lee, et al. 2001. Phytother. Res., 15(1):39-43.
Chevallier, A, The Encyclopedia of Medicinal Plants (Horn V. and Weil, C., Eds.) Dorling Kindersley Ltd., London (1996).
Noda, Y and Mori, A, Antioxidant Activities of Uyaku (Lindera Strychnifolia) Leaf Extract: A Natural Extract Used in Traditional Medicine. 2006.

\* cited by examiner

HERBAL COMPOSITIONS FOR THE PREVENTION OR TREATMENT OF URINARY INCONTINENCE AND OVERACTIVE BLADDER

RELATED PATENT APPLICATIONS

This application is a continuation of U.S. patent application Ser. No. 13/725,381, filed Dec. 21, 2012, now U.S. Pat. No. 9,452,191 which claims the benefit of and priority to U.S. Provisional Patent Application Ser. No. 61/580,125, filed Dec. 23, 2011, all of which are incorporated herein by reference in their entirety. All publications, patents, and patent applications cited in this Specification are also hereby incorporated by reference in their entirety.

GENERAL BACKGROUND

Urinary incontinence (UI) with urinary urgency and/or frequency and Overactive Bladder (OAB) are common problems affecting one in five people in the United States. The total affected population is difficult to quantify as it is often under-reported. NIH and the Simon Foundation estimates suggest that between 17 and 33 million people in the United States are affected. NAFC (National Association for Continence) estimates on the basis of multiple studies and expert opinion that 25 million adult Americans experience transient or chronic urinary incontinence.

Bladder weakness affects 25% of reproductive age women, 50% of post-menopausal women, and 50%-75% of women in nursing homes. In men, 60% over the age of 60 experience benign prostate enlargement and associated OAB symptoms. Bladder problems remain under-diagnosed and under-reported.

Bladder control problems can occur for many reasons. Temporary bladder control problems may be caused by, for example, urinary tract infections, vaginal infections or irritation, constipation, and certain medicines. Longer lasting or chronic incontinence can be caused by, for example, both overactive and weak bladder muscles, obstruction from an enlarged prostate, damage to nerves that control the bladder from diseases such as multiple sclerosis or Parkinson's disease, or diseases such as arthritis that can make walking painful and slow.

The basic types of bladder control problems include urinary urgency, urinary frequency, incontinence (bladder accidents with involuntary loss of urine) and nocturia (having to get out of bed at night for the toilet). Overactive bladder in many cases refer to both urinary frequency and urgency.

There are multiple types of urinary incontinence, which include, for example, stress incontinence, urge incontinence, overflow incontinence, and functional incontinence. Stress incontinence happens when urine leaks during exercise, coughing, sneezing, laughing, lifting heavy objects, or other body movements that put pressure on the bladder. It is the most common type of bladder control problem in younger and middle-age women. In some cases, it is related to the effects of childbirth. It may also begin around the time of menopause.

In some embodiments, urge incontinence can happen when a person cannot hold his or her urine long enough to get to the toilet in time. Healthy people can have urge incontinence, but it is often found in people who have diabetes, stroke, Alzheimer's disease, Parkinson's disease, or multiple sclerosis. It is also sometimes an early sign of bladder cancer.

In some embodiments, overflow incontinence can happen when small amounts of urine leak from a bladder that is always full. A man can have trouble emptying his bladder if an enlarged prostate is blocking the urethra. Diabetes and spinal cord injury can also cause this type of incontinence. Functional incontinence can happen in many older people who have normal bladder control. They have a hard time getting to the toilet in time because of arthritis or other disorders that make moving quickly difficult.

Medical treatments for bladder control problems, UI, and OAB can include physical and behavioral therapies, such as Kegel's pelvic floor exercises and bladder retraining; drug medications; devices such as catheters; and surgery may also be an option for some sufferers. Current drug therapies include anticholinergics (with antispasmodic effects, e.g., oxybutinin), smooth muscle relaxants (antispasmodics), tricyclic antidepressants (e.g., imipramine), alpha-adrenergic antagonists, alpha-adrenergic agonists (e.g., phenylpropanolamine), prostaglandin synthesis inhibitors, calcium channel blockers and others (Sullivan and Abrams, Eur. Urol., 36 Suppl 1:89-95 (1999); Andersson, Baillieres Best Pract. Res. Clin. Obstet. Gynaecol., 14(2): 291-313 (2000); Owens and Karram, Drug Saf, 19(2): 123-39 (1998); Wada et al., Arch. Int. Pharmacodyn Ther., 330(1): 76-89 (1995)). Unfortunately, most drug treatments are associated with unpleasant side effects, and this affects on patient compliance (Sullivan and Abrams, Eur. Urol., 36 Suppl 1: 89-95 (1999); Andersson, Baillieres Best Pract. Res. Clin. Obstet. Gynaecol., 14(2): 291-313 (2000); Owens and Karram, Drug Saf., 19(2):123-39 (1998); Wada et al., Arch. Int. Pharmacodyn Ther., 330(1): 76-89 (1995))2-5.

Acetylcholine is the primary excitatory neurotransmitter involved in bladder emptying. Certain drugs commonly prescribed for urinary incontinence, such as oxybutynin hydrochloride, inhibit the muscarinic action of acetylcholine on smooth muscle, producing a direct antispasmodic action. These drugs relax the detrusor muscle. Wada Y. et al., Arch. Int. Pharmacodyn. Ther., 330(1):76-89 (1995); Tapp A. J. S. et al., Brit. J. Obstetrics Gynecology, 97: 521-6 (1990). These medications also produce unwanted anticholinergic effects, such as dry mouth, blurred vision and constipation. Pathak A S, Aboseif S R. Overactive Bladder: Drug therapy versus nerve stimulation. Nat Clin Pract Urol, 2(7): 310-311, 2005; Wein (2001). Natural therapies have also been investigated for this condition (Steels et al., Aust. Continence J., 7(2): 34-37 (2001); Karantanis et al., Aust. Continence J., 6(4): 6-7 (2000); Arya et al., Obstetrics and Gynecology, 96(1): 85-89 (2000); Bryant et al., Aust. Continence J., 6(4): 8 (2000)). In Ayurveda, *Crateva nurvala* is a drug highly regarded for its use in the management of uropathies (Nadkarni, Indian Materia Medica. Bombay Popular Prakashan). Western traditional treatments recommend the use of *Equisetum arvense* (British Herbal Pharmacopeia. Publ: British Herbal Medicine Association 1983). Chinese medicine values *Lindera* for its various properties (Bensky D and Gamble A, 1993. Chinese Herbal Materia Medica, Revised Edition. England Press, Seattle, Wash., USA.)

Isolated clinical studies conducted using herb-based natural therapies for urinary incontinence include *Crateva nurvala* herb, acupuncture and dietary intervention such as modification of dietary intake. Deshpande et al., Indian J. Med. Res. 76(supp): 46-53, 1982; Karantanis et al., Aust. Continence J., 6(4): 6-7, 2000; Arya et al., Obstetrics and Gynecology, 96(1): 87-89, 2000; Bryant et al., Aust. Continence J., 6(4): 8, 2000.

In some embodiments, overactive bladder (OAB) is a condition that can be characterized by the sudden need to urinate. If that need results in the unintentional leakage of urine, the condition is called urge incontinence ("OAB wet"). Thus, urge incontinence falls within the general definition of OAB in some embodiments. In some embodiments, OAB can result from the sudden, involuntary contraction of the muscle in the wall of the urinary bladder. Approximately one-third of people with OAB also experience urge incontinence ("OAB wet"), while approximately two-thirds have OAB without urge incontinence ("OAB dry"). According to the National Overactive Bladder Evaluation, OAB affects 16.5% of the population, with 16.9% of women and 16.0% of men affected. Stewart et al., World J. Urol. 20: 327-336, (2003). OAB, like urinary incontinence, is treated primarily with anticholinergic drugs (e.g., oxybutinin). These inhibit the neurotransmitter acetylcholine from attaching to the bladder muscle, and thereby reduce the frequency and intensity of contractions of the bladder. Unfortunately, adverse side effects of these drugs include dry mouth, dry eyes, constipation, and headache. Anderson, Urology, 3A: 32-41 (2004); Cruz, Urology. 3A: 65-73 (2004); Appell et al., Mayo Clinical Proc., 78:696-702. (2003).

There are currently no medications that specifically target incontinence or OAB symptoms without having side effects elsewhere in the body. Herbal approaches to bladder problems that improve the tone and tissue strength of the bladder and surrounding area are proving to be effective for bladder control problems. (See, U.S. Pat. No. 7,378,115; and Schauss A G, Spiller G, Chaves S, Gawlicka A, 2006. Reducing the symptoms of overactive bladder and urinary incontinence: results of a two-month, double-blind, placebo-controlled clinical trial. Poster presentation FASEB, San Francisco, April, 2006.) The timeframe for these herbal preparations to produce effective improvements in bladder control is two to three months. In may instances, the length of time before effective results are experienced can result in distress and discomfort for the patient, as well as an expected reduction in patient compliance with the treatment. Herbal treatments that produce results within a shorter timeframe are warranted.

Thus, a need exists for the identification of new herb-containing compositions that can provide effective prevention or treatment of urinary incontinence and overactive bladder.

SUMMARY

One embodiment described herein is related to herbal compositions useful for the prevention or treatment of urinary incontinence and overactive bladder. The herb-containing compositions provide herein can be formulated in a dry delivery system, liquid delivery system, or a controlled-release vehicle. In one embodiment, the herb-containing compositions are formulated as oral dosage units which include a tablet; dry powder; capsule; and caplet.

One embodiment provides an herb-containing composition, comprising (i) a *Crateva nurvala* extract preparation; (ii) an *Equisetum arvense* extract preparation; and (iii) a *Lindera aggregata* extract preparation; wherein the herb-containing composition is formulated as an oral dosage unit.

An alternative embodiment provides an herb-containing composition, comprising: (i) a *Crateva nurvala* stem/bark extract preparation present; (ii) an *Equisetum arvense* stem extract preparation; (iii) a *Lindera aggregata* root extract preparation; wherein the herb-containing composition is formulated as an oral dosage unit, and wherein the *Equisetum arvense* stem extract preparation and the *Lindera aggregata* root extract preparation are present at the same concentration.

An effective daily amount of each herb ranges from about 1 g to 18 g *Crateva nurvala*, about 750 mg to 12 g *Equisetum arvense* and about 750 mg to 12 g *Lindera aggregata*. In an alternative embodiment, an effective daily amount of each herb ranges from about 3 g to 12 g *Crateva nurvala*, about 1.5 g to 6 g *Equisetum arvense* and about 1.5 g to 6 g *Lindera aggregata*. In another alternative embodiment, an effective daily amount of each herb ranges from about 4 g to 8 g *Crateva nurvala*, about 2 g to 4 g *Equisetum arvense* and about 2 g to 4 g *Lindera aggregata*. In another alternative embodiment, an effective daily amount of each herb contains about 6 g *Crateva nurvala*, about 3 g *Equisetum arvense* and about 3 g *Lindera aggregata*.

In an alternative embodiment, the effective daily amount is taken in two equivalent doses. For example, in one embodiment, each dose contains about 3 g *Crateva nurvala*, about 1.5 g *Equisetum arvense* and about 1.5 g *Lindera aggregata*.

In another alternative embodiment, the effective daily amount is taken in three equivalent doses. For example, in one embodiment, each doses contains about 2 g *Crateva nurvala*, about 1 g *Equisetum arvense* and about 1 g *Lindera aggregata*.

An alternative embodiment provides an herb-containing composition with at least one of the herbal components is a standardized preparation. In an alternative embodiment, the herb-containing composition has two of the herbal components as standardized preparations. In another embodiment, all three herbal components of the herb-containing composition (*Crateva nurvala, Equisetum arvense* and *Lindera aggregata*) are standardized preparations.

An alternative embodiment provides a kit for the prevention or treatment of the symptoms of urinary incontinence or overactive bladder comprising *Crateva nurvala, Equisetum arvense* and *Lindera aggregata*, each separately in the form of a tablet. In an alternative embodiment, two or three herbs are combined in a single tablet. In an alternative embodiment, the kit comprises sufficient tablets for the prevention or treatment of the symptoms of urinary incontinence or overactive bladder in a subject for 30 days. In alternative embodiments, the kit comprises sufficient tablets for the prevention or treatment of the symptoms of urinary incontinence or overactive bladder in a subject for 7, 14, 21, or 28 days. In another alternative embodiment, the kit comprises a sufficient number of tablets for the prevention or treatment of the symptoms of urinary incontinence or overactive bladder in a subject for 2, 3, 4, 5, 6, 9, or 12 months.

Another embodiment provides a method for the prevention or treatment of the symptoms of urinary incontinence or overactive bladder. The method comprises administering an herb-containing composition to a subject in need thereof, the herb-containing composition comprising: (i) a *Crateva nurvala* stem/bark extract preparation; (ii) an *Equisetum arvense* stem extract preparation; and (iii) a *Lindera aggregata* root extract preparation; wherein the herb-containing composition is formulated as an oral dosage unit.

DRAWINGS

The invention will be more fully understood by reference to the following drawings, which are for illustrative purposes only:

DETAILED DESCRIPTION

Figure 1:
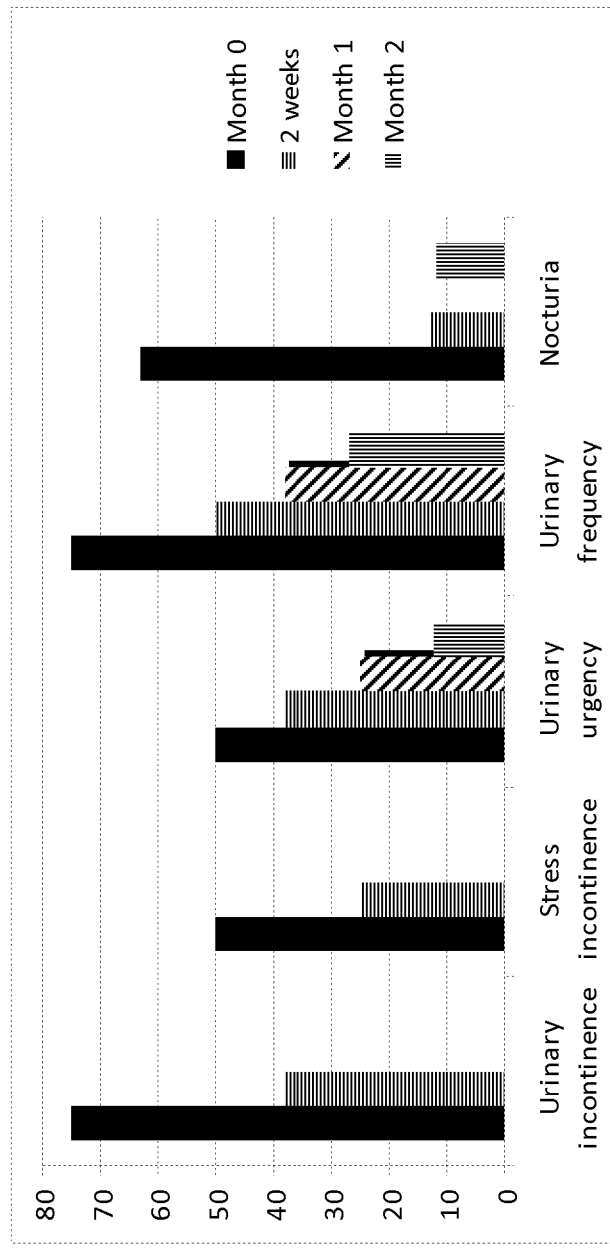
FIG. 1 is a histogram graph showing the percentage (%) of participant population affected by symptoms of urinary incontinence and overactive bladder during clinical assessment in one embodiment.

It is to be appreciated therefore that certain aspects, modes, embodiments, variations and features of the invention described below in various levels of detail in order to provide a substantial understanding of the present invention. In general, such disclosure provides beneficial herb-containing compositions, combinations of such compositions with other dietary supplement compositions, and related methods of producing and using same.

Accordingly, the various aspects of the present invention relate to therapeutic or prophylactic uses of certain particular herb-based compositions in order to prevent or treat a disease, injury or condition related to urinary incontinence. Accordingly, various particular embodiments that illustrate these aspects follow.

It is to be appreciated that the various modes of treatment or prevention of medical conditions as described are intended to mean "substantial", which includes total but also less than total treatment or prevention, and wherein some biologically or medically relevant result is achieved.

A "subject" as described in some embodiments herein can be a mammal, such as a human, but can also be an animal, such as domestic animals (e.g., dogs, cats and the like), farm animals (e.g., cows, sheep, pigs, horses and the like), and laboratory animals (e.g., rats, mice, guinea pigs and the like).

An "effective amount" of a composition as described in some embodiments herein can be a quantity sufficient to achieve a desired therapeutic and/or prophylactic effect, for example, an amount which results in the prevention of, or a decrease in the symptoms associated with, a disease that is being treated. The amount of composition administered to the subject, particularly one in need of the composition, can depend on the type and severity of the disease and on the characteristics of the individual, such as general health, age, sex, body weight and tolerance to drugs. It can also depend on the degree, severity and type of disease. A skilled artisan will be able to determine appropriate dosages depending on these and other factors. Typically, an effective amount of the compositions described herein can be sufficient for achieving a therapeutic or prophylactic effect.

In some embodiments, it can be advantageous to formulate oral compositions in dosage unit form for ease of administration and uniformity of dosage. Dosage unit forms described in some embodiments can refer to physically discrete units suited as unitary dosages for the subject to be treated; each unit containing a predetermined quantity of active composition calculated to produce the desired therapeutic effect in association with the suitable pharmaceutical carrier. The specification for the dosage unit forms provided in one embodiment may be dictated by and directly dependent on the characteristics of the dietary supplement and the particular therapeutic effect to be achieved, and the limitations inherent in the art of producing such an active composition for the treatment of individuals. The pharmaceutical compositions can be included in a container, pack, or dispenser, together with instructions for administration. Generally, in some embodiments an oral dose is taken two-times to four-times daily, until symptom relief is apparent. The compositions provided herein can also be administered in combination with each other, or with one or more additional therapeutic compositions.

Herbal Ingredients

*Crateva nurvala* (or "*C. nurvala*") is a moderate-sized tree attaining a height of over 15 meters; it is named after crateuas (Krateuas), a Greek naturalist and physician of the first Century B.C. Common throughout India, the much-branched tree with a head of glossy trifoliate leaves looks very majestic when in full bloom from March to May (earlier in the South). The bark of the tree is reported to be used as a demulcent, antipyretic, sedative, alterative and tonic.

*Equisetum arvense* (or "*E. arvense*") (botanical synonyms and common names include, for example, Horsetail; Shavegrass; Bottle-brush; Paddock-pipes; Dutch Rushes; Pewterwort; Shavegrass; Pewterwort; Bottlebrush; Horsetail rush; Paddock-pipes; Dutch rushes; Mare's tail) is a European herb that grows in moist waste places throughout temperate regions of the world and is cultivated in Yugoslavia. This perennial plant is common to moist loamy or sandy soil all over North America and Eurasia. Compared to the other herbs in the plant kingdom, horsetail is very rich in silicon. *Equisetum* is used medicinally. The sterile stems are harvested in summer and dried. The barren stems are useful as medicine, appearing after the fruiting stems have died down, and are used in their entirety, cut off just above the root. The herb is used either fresh or dried, but can be most efficacious when fresh in one embodiment. A fluid extract is prepared from it. The ashes of the plant are also employed.

*Lindera aggregata* (or "*L. aggregata*") (botanical synonyms and common names include *Lindera strychnifolia*, Japanese evergreen spicebush, Chinese allspice, Evergreen *Lindera*, Kosterm, Uyaku (Japanese), Oyak (Korean)) is a Chinese herb grown in locations including Zhejiang, Hunan, Anhui, Guangdong, and Guangxi. (Bensky and Gamble). *Lindera* is an evergreen Shrub growing to 9 m (29 ft 6 in). The flowers are dioecious (i.e., individual flowers are either male or female, but only one sex is to be found on any one plant so both male and female plants must be grown if seed is needed). The plant is not self-fertile. The plant tends to prefer light (sandy), medium (loamy) and heavy (clay) soils, preferring moist soil. The plant tends to prefer acid and neutral soils and can grow in very acid soils and in semi-shade (light woodland). It can be harvested in winter or spring (Bensky and Gamble). The root and leaves are used therapeutically.

Herbs are useful in various forms, for example, as a homogenized mixture obtained by grinding or chopping a herb. The herbs are optionally subjected to processing such as extractions, for example by obtaining a filtrate by filtering or a supernatant by centrifugation. Known methods are readily used to extract a leaf, root, seed, stem, bark etc as appropriate. In certain embodiments, extracts that contain purified active ingredients are prepared. An isolated active ingredient is an ingredient purified from *C. nurvala*, *E.*

*arvense* and *L. aggregata* that has activity to control (i.e., typically reduce) the symptoms UI/OAB in a subject. Administration or use of an isolated active ingredient of another herb of the compositions herein, is considered to be a use or administration of the herb itself. The inventor has identified certain compounds in the herbs above without wishing to be bound by theory about compounds and metabolites in the herbs and mechanisms of how the herbs in the compositions herein control the symptoms UI/OAB.

In one embodiment, the *C. nurvala* herb preparation can be extracted from the stem and/or bark of the plant, and the preparation is present at a concentration at least about 3,000 mg dry weight equivalents per oral dosage unit. That is, the starting material is 3,000 mg of *C. nurvala* dry stem/bark. This starting material is eventually concentrated during the manufacturing process to a ratio ("extract ratio") of at least about 5 (i.e., 5:1), such as at least about 10, such as at least about 20, such as at least about 25, such as at least about 30, such as at least about 35, such as at least about 40. In one embodiment, the ratio is between about 25 and about 35. As an illustrative example, a ratio of 10 would be equivalent to 300 mg of *C. nurvala* preparation. Accordingly, 300 mg of *C. nurvala* stem/bark preparation (which is concentrated) is equivalent to 3,000 mg dry weight of *C. nurvala* stem/bark or 3,000 mg of *C. nurvala* dry stem/bark starting material. In one embodiment, the *C. nurvala* herb preparation is derived from the stem and/or bark parts of the *C. nurvala* herb, i.e., a *C. nurvala* stem/bark extract preparation.

The *E. arvense* herb preparation can be extracted from the stem of the plant, and the preparation is present at a concentration of at least about 1,500 mg dry weight equivalents per oral dosage unit. That is, the starting material is 1,500 mg of *E. arvense* herb. This starting material is eventually concentrated during the manufacturing process to an extract ratio of at least about 5, such as at least about 8, such as at least about 10, such as at least about 15. As an illustrative example, a ratio of 4 or 5 would be equivalent to 375 mg or 300 mg, respectively, of *E. arvense* herb preparation. Thus, in the case of a concentration ratio of 5, for example, 300 mg of *E. arvense* herb preparation (which is concentrated) is equivalent to 1,500 mg dry weight of *E. arvense* herb or 1,500 mg of *E. arvense* dry herb starting material. In one embodiment, the *E. arvense* herb preparation is derived from the stem parts of the *E. arvense* herb, i.e., a *E. arvense* stem extract preparation.

The *L. aggregata* herb preparation can be extracted from the stem of the plant, and the preparation is present at a concentration of at least about 1,500 mg dry weight equivalents per oral dosage unit. That is, the starting material is 1,500 mg of *L. aggregata* herb. This starting material is eventually concentrated during the manufacturing process to an extract ratio of at least about 5, such as at least about 8, such as at least about 10, such as at least about 15. As an illustrative example, a ratio of 4 or 5 would be equivalent to 375 mg or 300 mg, respectively, of *L. aggregata* herb preparation. Thus, in the case of a concentration ratio of 5, for example, 300 mg of *L. aggregata* herb preparation (which is concentrated) is equivalent to 1,500 mg dry weight of *L. aggregata* herb or 1,500 mg of *L. aggregata* dry herb starting material. In one embodiment, the *L. aggregata* herb preparation is derived from the root parts of the *L. aggregata* herb, i.e., a *L. aggregata* root extract preparation.

In some embodiments, the herbal ingredients described herein, alone or in combination, can provide the following remedy or support:

Bladder Support

*Crateva nurvala*, an Ayurvedic herb, has been used for many centuries for urinary support and to help with diseases of the bladder.[1] It has tonic effects on the bladder and is recommended for poor bladder tone and symptoms of incontinence.

Kidney/Bladder Stones

*Crateva* and Horsetail balance urinary minerals and reduce the likelihood of stone formation.[2,3] A key constituent of *Crateva*, lupeol, has been shown in a number of studies to have anti-oxaluric and anti-calcuric effects leading to increased spontaneous passing of these two most common forms of stones as well as symptomatic relief.[2,4,5] Horsetail constituents inhibit xanthine oxidase and subsequent urate calculi formation.[7] It is thought that this effect is promoted by a tonic contractile effect of *Crateva* and Horsetail on the smooth muscle, which also assists with bladder control.[1,2,4]

Incontinence/OAB

*Crateva* and Horsetail help to improve the tone of the bladder wall. *Crateva* has beneficial effects on neurogenic bladder and post-prostatectomic atony of the bladder.[1] *Crateva* is shown to produce a significant reduction in urinary symptoms of frequency, incontinence, pain and retention of urine in men with hypotonic bladder as a result of benign prostatic hypertrophy. *Crateva* acts to increase the tone of the bladder and the expulsive force of urine, thereby helping effective evacuation.[1] *Crateva* normalizes the tone of the urinary bladder and significantly decreases residual urine volume.

Animal studies support this. *Crateva* has been shown to increase the tone of both smooth and skeletal muscle in vitro.[6] Forty days of treatment produced dramatic improvement.

Research also supports the effectiveness of the combined *Crateva* and Horsetail for bladder control.[8,9] This combination showed improvements in bladder emptying frequency, leakage, urgency and bladder pain or discomfort with best results occurring after two to three months of treatment.[8,9]

*Lindera* has a long history of use in Traditional Chinese Medicine for kidney and bladder health and is specific for frequent urination and loss of bladder control.[21,22] *Lindera* is also recommended for the treatment of renal disease.[21]

Quality of Life

Poor bladder control is shown to negatively affect emotional health and to reduce quality of life for the sufferer.[10,11] Research has shown the *Crateva* and Horsetail combined significantly improved quality of life measurements including feeling less frustration, increased social activities, and better travel.[8,9]

Anti-Inflammatory

All of three herbs described herein show anti-inflammatory effects.[12-18] *Crateva* and *Lindera* have anti-inflammatory and antibacterial properties.[12-18] The positive effect on chronic urinary tract infections is most likely a combination of anti-bacterial and anti-inflammatory actions.

Kidney Protective

*Crateva* and *Lindera* are also shown to have kidney protective effects; *Crateva* has been shown to be nephroprotective in rats exposed to toxic doses of cadmium, while *Lindera* preserves renal function in animals with diabetic nephropathy.[19,20]

Animal research demonstrates that *Lindera* slows the progression of diabetic nephropathy (destruction of the kidneys that can occur as a complication of diabetes) and could therefore be used as a preventative approach to protect renal function from deterioration.[20] Use of *Lindera* can result in improved renal function, as evaluated by creatinine clearance and serum creatinine. Kidneys of the *Lindera* treated group showed glomeruli with greater area and cell population.

Anti-Oxidant/Anti-Aging

More recent research has shown that *Lindera* has potent antioxidant effects to preserve tissue and function of urinary system. It has potent antioxidant scavenging activity against ROS and RNS (reactive oxygen species and reactive nitrogen species—both common oxidants that damage body tissues) that effectively inhibits lipid peroxidation.[23] *Lindera* extracts show protection against neuronal oxidative injury and may be of benefit to protect against neuronal Central nervous system degeneration.[24] *Lindera* also has antibacterial effects.[21]

Joint Support

*Lindera* is also used traditionally for rheumatic complaints, and multiple studies have shown that *Lindera* or *Lindera* extracts reduce inflammation.[15-17] Alkaloids derived from *Lindera* have been shown in animal studies to have anti-inflammatory effects and to be of benefit for rheumatoid arthritis (RA).[15] *Lindera* has also been shown to inhibit the effects of inflammatory mediators from macrophages. These help illustrate therapeutic efficiency on the inflammation and joint destruction in RA.[16] This supports the use of *Lindera* for analgesic and anti-inflammatory actions to improve symptoms of RA and protect joints from destruction.[17]

Cardiovascular Support

*Lindera* is traditionally recommended for the treatment of cardiac support. Animal studies have shown that *Lindera* can improve heart function.[22]

Herb-Containing Compositions

One embodiment described herein provides herb-containing compositions useful in a method of prophylaxis or treatment of disorders of the urogenital system—e.g., urinary incontinence, enuresis (e.g., bed-wetting), benign prostatic hyperplasia, overactive bladder, nocturia, urinary calculi, cystitis, and urinary tract infection (or "UTI"). In particular, one embodiment provides a composition, which contains *C. nurvala, E. arvense*, and *L. aggregata*; in one embodiment the composition is useful in the prevention and treatment of disorders of the urogenital system. In one embodiment, the herb-containing composition contains *C. nurvala* extract preparation, *E. arvense* extract preparation, and *L. aggregata* preparation.

In one embodiment, the herb-containing composition is an oral supplement included in a dry delivery system, e.g., tablet, dry powder, and dry meal replacement mixture. In another embodiment, the herb-containing composition is an oral supplement included in a liquid delivery system, e.g., capsule, caplet, or beverage. In another embodiment, the herb-containing composition is an oral supplement included in a controlled-release vehicle, e.g., tablet, caplet, and capsule.

In one embodiment, the herb-containing composition contains from about 1,000 mg to about 6,000 mg dry weight equivalents *C. nurvala* stem/bark extract per oral dosage unit. In another embodiment, the herb-containing composition contains from about 1,000 mg to about 4,000 mg dry weight equivalents *C. nurvala* stem/bark extract per oral dosage unit. In another embodiment, the herb-containing composition contains from about 2,500 mg to about 3,500 mg dry weight equivalents *C. nurvala* stem/bark extract per oral dosage unit. In one embodiment, the herb-containing composition contains about 3,000 mg dry weight equivalents *C. nurvala* stem/bark extract per oral dosage unit. A *C. nurvala* stem/bark extract is an extract prepared using both the stem parts and bark of the *C. nurvala* herb.

In another embodiment, the herb-containing composition contains from about 1,000 mg to about 6,000 mg dry weight equivalents *C. nurvala* stem extract per oral dosage unit. In another embodiment, the herb-containing composition contains from about 1,000 mg to about 4,000 mg dry weight equivalents *C. nurvala* stem extract per oral dosage unit. In another embodiment, the herb-containing composition contains from about 2,500 mg to about 3,500 mg dry weight equivalents *C. nurvala* stem extract per oral dosage unit. In one embodiment, the herb-containing composition contains about 3,000 mg dry weight equivalents *C. nurvala* stem extract per oral dosage unit.

In another embodiment, the herb-containing composition contains from about 1,000 mg to about 6,000 mg dry weight equivalents *C. nurvala* bark extract per oral dosage unit. In another embodiment, the herb-containing composition contains from about 1,000 mg to about 4,000 mg dry weight equivalents *C. nurvala* bark extract per oral dosage unit. In one embodiment, the herb-containing composition contains from about 2,500 mg to about 3,500 mg dry weight equivalents *C. nurvala* bark extract per oral dosage unit. In one embodiment, the herb-containing composition contains about 3,000 mg dry weight equivalents *C. nurvala* bark extract per oral dosage unit.

In one embodiment, to prepare the herb-containing composition, the bark and/or stems of *C. nurvala* are isolated from the rest the *C. nurvala* plant and dried. The dried bark and stems of *C. nurvala* are extracted using 70% ethanol/water. The liquid extract is then concentrated to a ratio of 10:1. Maltodextrin is used as an excipient. The final product, i.e., *C. nurvala* stem/bark extract, used in the herb-containing composition is a brown to dark brown powder. In an alternative embodiment, the liquid extract is then concentrated to a ratio of between about 25 and 35. Maltodextrin is used as an excipient.

In one embodiment, the *E. arvense* herb preparation component of the herb-containing composition is derived from the leaf of the *E. arvense* herb. In one embodiment, the *E. arvense* herb preparation component of the herb-containing composition is derived from the stem of the *E. arvense* herb. In another embodiment, the *E. arvense* herb preparation component of the herb-containing composition is derived from a mixture of plant parts of the *E. arvense* herb. In another embodiment, the *E. arvense* herb preparation component of the herb-containing composition is derived from all the parts of the plant that extend above-ground. In one embodiment, the herb-containing composition contains from about 1 mg to about 3,000 mg dry weight equivalents *E. arvense* herb preparation per oral dosage unit. In another embodiment, the herb-containing composition contains from about 500 mg to about 2,500 mg dry weight equivalents *E. arvense* herb preparation per oral dosage unit. In another embodiment, the herb-containing composition contains from about 1,000 mg to about 2,000 mg dry weight equivalents *E. arvense* herb preparation per oral dosage unit. In another embodiment, the herb-containing composition contains from about 1,300 mg to about 1,600 mg dry weight equivalents *E. arvense* herb preparation per oral dosage unit. In one embodiment, the herb-containing composition contains about 1,500 mg dry weight equivalents *E. arvense* stem extract per oral dosage unit.

In one embodiment, the *L. aggregata* herb preparation component of the herb-containing composition is derived from the roots of the *L. aggregata* herb. In one embodiment, the *L. aggregata* herb preparation component of the herb-containing composition is derived from the leaf and/or stem of the *L. aggregata* herb. In another embodiment, the *L. aggregata* herb preparation component of the herb-containing composition is derived from a mixture of plant parts of the *L. aggregata* herb. In another embodiment, the *L. aggregata* herb preparation component of the herb-containing composition is derived from all the parts of the plant that extend above-ground and/or below-ground. In one embodiment, the herb-containing composition contains from about 1 mg to about 3,000 mg dry weight equivalents *L. aggregata* herb preparation per oral dosage unit. In another embodiment, the herb-containing composition contains from about 500 mg to about 2,500 mg dry weight equivalents *L. aggregata* herb preparation per oral dosage unit. In another embodiment, the herb-containing composition contains from about 1,000 mg to about 2,000 mg dry weight equivalents *L. aggregata* herb preparation per oral dosage unit. In another embodiment, the herb-containing composition contains from about 1,300 mg to about 1,600 mg dry weight equivalents *L. aggregata* herb preparation per oral dosage unit. In some embodiments, the *L. aggregata* herb preparation can be present at a comparable, such as the same, concentration as the *E. arvense* preparation. In one embodiment, the herb-containing composition contains about 1,500 mg dry weight equivalents *L. aggregata* root extract per oral dosage unit.

In some instances, silicon is identified as a contributor to the biological activity of *E. arvense* herb. Non-standardized preparations of *E. arvense* herb generally contain silicon from about 1.2% to about 6.9% silicon based on total dry weight of preparation. In one embodiment, it has been determined that batch variation in the silicon content of *E. arvense* herb preparations can have negative effects on the biological activity of the composition described herein. This problem can be resolved in one embodiment by providing an *E. arvense* herb preparation with optimized, standardized silicon content. Accordingly, in one embodiment, the silicon content of the *E. arvense* herb preparation in the herb-containing preparation can be standardized. The use of a standardized preparation *E. arvense* herb can be advantageous because the inter-batch variation of silicon can be reduced, thus the composition described herein can yield more consistent preventative or therapeutic effect. In one embodiment, the *E. arvense* herb preparation is standardized to contain from about 3% silicon to about 13% silicon based on the total dry weight of the *E. arvense* herb preparation. In another embodiment, the *E. arvense* herb preparation is standardized to contain from about 5% silicon to about 10% silicon based on the total dry weight of the *E. arvense* herb preparation. In another embodiment, the *E. arvense* herb preparation is standardized to contain at least about 6% silicon based on the total dry weight of the *E. arvense* herb preparation.

In addition to silicon, *E. arvense* contains about 5 percent of a saponin, designated equisetonin, and several flavone glycosides (i.e., flavonoids) including isoquercetrin, galuteolin, and equisetrin. Isoquercetrin (i.e., isoquercitrin; Quercetin 3-O-β-D-glucopyranoside; 4H-1-Benzopyran-4-one, 2-(3,4-di hydroxy-phenyl)-3-(β-D-glucofuranosyloxy)-5,7-dihydroxy-). Flavonoids, e.g., isoquercetrin, may have important pharmacological properties. Many flavonoids are diuretic, some are antispasmodic, anti-inflammatory, antiseptic and even antitumor. However, the predominant action of the flavonoids as a group is on the vascular system. The flavone glycosides and the saponin likely combine to account for the diuretic action of *E. arvense*.

One embodiment provides an herb-containing composition, comprising: a *C. nurvala* stem/bark preparation present at a concentration at least about 3,000 mg dry weight equivalents per oral dosage unit; an *E. arvense* stem extract preparation at a concentration of at least about 1,500 mg dry weight equivalents per oral dosage unit; and a *L. aggregata* root extract preparation at a concentration of at least about 1,500 mg dry weight equivalents per oral dosage unit. Optionally, the composition can further comprise a total silicon concentration of at least about 32.5 mg dry weight equivalents per oral dosage unit; a phosphorus concentration of at least about 24.9 mg dry weight equivalents per oral dosage unit; a magnesium concentration of at least about 14.5 mg dry weight equivalents per oral dosage unit; and a calcium concentration of at least about 16.3 mg dry weight equivalents per oral dosage unit.

Another embodiment provides an herb-containing composition, comprising a *C. nurvala* stem/bark preparation, an *E. arvense* stem extract preparation with a total flavonoid content from about 0.01% to about 3% total flavonoids based on the total dry weight of the *E. arvense* preparation, and a *L. aggregata* root extract preparation; wherein the total flavonoid content is expressed as isoquercetrin and wherein the herb-containing composition is formulated as an oral dosage unit. In one embodiment, the *E. arvense* herb preparation can be a standardized *E. arvense* stem extract preparation. In one embodiment, the standardized *E. arvense* herb preparation further comprises a total flavonoid content from about 0.1% to about 2.5% total flavonoids based on the total dry weight of the *E. arvense* preparation and expressed as isoquercetrin. In one embodiment, the standardized *E. arvense* herb preparation comprises a total flavonoid content from about 0.5% to about 1.5% total flavonoids based on the total dry weight of the *E. arvense* preparation, wherein the total flavonoid content is expressed as isoquercetrin. In one embodiment, the standardized *E. arvense* herb preparation comprises a total flavonoid content from at least about 0.8% total flavonoids based on the total dry weight of the *E. arvense* preparation, wherein the total flavonoid content is expressed as isoquercetrin.

Other embodiments of the herbal composition are presented in Table 1.

TABLE 1

Ranges of effective daily amounts of the herbal composition

| Component | Range A (g/day) | Range B (g/day) | Range C (g/day) |
|---|---|---|---|
| C. nurvala | 1-18 | 3-12 | 4-8 |
| E. arvense | 0.75-12 | 1.5-6 | 2-4 |
| L. aggregate | 0.75-12 | 1.5-6 | 2-4 |

An alternative embodiment provides an herb-containing composition with at least one of the herbal components is a standardized preparation. In an alternative embodiment, the herb-containing composition has two of the herbal components as standardized preparations. In another embodiment, all three herbal components of the herb-containing composition (*Crateva nurvala*, *Equisetum arvense* and *Lindera aggregata*) are standardized preparations. Various embodiments of the standardized preparations are provided in Table 2. For example, in alternative embodiment A, all three herbs are non-standardized, while in embodiment G, all three herbs are standardized.

TABLE 2

Various embodiments of the standardized preparations of the herbal composition

| Embodiment | C. nurvala | E. arvense | L. aggregata |
|---|---|---|---|
| A | — | — | — |
| B | * | — | — |
| C | — | * | — |
| D | — | — | * |
| E | * | * | — |
| F | — | * | * |
| G | * | * | * |

NOTE:
Herbs denoted with an asterisk (*) are standardized; herbs denoted with a dash (—) are non-standardized.

One embodiment provides a pharmaceutical composition comprising the herb-containing composition and a pharmaceutically-acceptable carrier.

Standardization

In some embodiments, it has been determined that batch variation in the silicon content and/or flavonoid content expressed as isoquercetrin of *E. arvense* herb preparations can have negative effects on the biological activity of the composition described herein. This problem has been resolved in some embodiments by providing *E. arvense* herb preparations with optimized, standardized silicon content and/or flavonoid content expressed as isoquercetrin. One embodiment provides an herb-containing composition, comprising a *C. nurvala* preparation, a *L. aggregata* preparation, and a standardized *E. arvense* herb preparation with a silicon content from about 3% to about 13% silicon based on total dry weight of the *E. arvense* preparation, wherein the herb-containing composition is formulated as an oral dosage unit. Accordingly, for 1,500 mg dry weight of *E. arvense* herb or 1,500 mg of *E. arvense* dry herb starting material, which produces 300 mg of *E. arvense* herb preparation (which is concentrated), a silicon content from about 3% to about 13% would represent approximately 9 to 39 mg silicon.

In one embodiment, the standardized *E. arvense* herb preparation further comprises a total flavonoid content from about 0.01% to about 3% total flavonoids based on the total dry weight of the *E. arvense* preparation, wherein the total flavonoid content is expressed as isoquercetrin. In one embodiment, the standardized *E. arvense* herb preparation further comprises a total flavonoid content from about 0.1% to about 2.5% total flavonoids based on the total dry weight of the *E. arvense* preparation and expressed as isoquercetrin. In one embodiment, the standardized *E. arvense* herb preparation further comprises a total flavonoid content from about 0.5% to about 1.5% total flavonoids based on the total dry weight of the *E. arvense* preparation, wherein the total flavonoid content is expressed as isoquercetrin. In one embodiment, the standardized *E. arvense* herb preparation further comprises a total flavonoid content from at least about 0.8% total flavonoids based on the total dry weight of the *E. arvense* preparation, wherein the total flavonoid content is expressed as isoquercetrin.

In another embodiment, it has been determined that batch variation in the total flavonoid content (expressed as isoquercetrin content) of *E. arvense* herb preparations can have negative effects on the biological activity of the composition described herein. This problem has been resolved in some embodiments by providing an *E. arvense* herb preparation with optimized, standardized total flavonoid content (expressed as isoquercetrin content). Accordingly, in one embodiment, the total flavonoid content (expressed as isoquercetrin content) of the *E. arvense* herb preparation in the herb-containing preparation is standardized. The use of a standardized preparation *E. arvense* herb is advantageous because the inter-batch variation of total flavonoid content (expressed as isoquercetrin content) is reduced, thus the composition provided herein can yield more consistent preventative or therapeutic effect. In one embodiment, the *E. arvense* herb preparation is standardized to contain from about 0.01% flavonoids to about 3% flavonoids based on the total dry weight of the *E. arvense* herb preparation, wherein the total flavonoids are expressed as isoquercetrin equivalents. In another embodiment, the *E. arvense* herb preparation is standardized to contain from about 0.1% flavonoids to about 2.5% flavonoids based on the total dry weight of the *E. arvense* herb preparation, wherein the total flavonoids are expressed as isoquercetrin equivalents. In another embodiment, the *E. arvense* herb preparation is standardized to contain from about 0.5% flavonoids to about 1.5% flavonoids based on the total dry weight of the *E. arvense* herb preparation, wherein the total flavonoids are expressed as isoquercetrin equivalents. In another embodiment, the *E. arvense* herb preparation is standardized to contain at least about 0.8% flavonoids based on the total dry weight of the *E. arvense* herb preparation, wherein the total flavonoids are expressed as isoquercetrin equivalents.

In one embodiment, the *E. arvense* herb preparation is standardized to organic silicon content by a solvent extraction process using raw material with a silicon content that met a minimum silicon content, e.g., 3% silicon. In one embodiment, the *E. arvense* herb preparation of the herb-containing composition is derived from the stems of the *E. arvense* herb and standardized for silica content (i.e., *E. arvense* stem extract preparation). Briefly, stem parts of the *E. arvense* herb are removed from the plant and dried. They are then measured for a minimum of 2.5% silicon content via HPLC analysis before being accepted for the extraction process. An extract was obtained using 65% (v/v) ethanol/water extraction solvent. The extract was concentrated to a ratio of approximately 4:1. The extract is then tested again for minimum 3% silicon content via HPLC. The final extract dry concentrate appeared as a fine brown powder with a characteristic odor and taste.

In another embodiment, the *E. arvense* herb preparation is standardized to organic silicon by a solvent extraction process. Briefly, stem parts of the *E. arvense* herb are removed from the plant and dried. Morphological examination of the starting biomass (this includes both microscopic and macroscopic characteristics) can help facilitate using the correct species (e.g., an authenticated voucher specimen is stored on file for species identification). An extract is obtained using hot water (between about 50° C. and about 100° C.) as a solvent. The extract is concentrated to a ratio of approximately 5:1. The extract is then dried. The extract is tested for a minimum of approximately 3% silicon content via UV-Vis Spectrophotometry (silicon dioxide is used as a reference substance). In one embodiment, if the extract falls outside the desired standards above, it is titrated with a dried extract that had undergone the same process as above. The final extract dry concentrate appear as a yellow-brown colored powder.

In one embodiment, the *E. arvense* herb preparation of the herb-containing composition is derived from the stems of the *E. arvense* herb and standardized for total flavonoid content, i.e., *E. arvense* stem extract preparation.

In another embodiment, the *E. arvense* herb preparation is standardized to flavonoid (expressed as isoquercetrin) content by a solvent extraction process. Briefly, stem parts of the

*E. arvense* herb are removed from the plant and dried. They are then identified by TLC. (isoquercetrin is used as reference substance). Morphological examination of the starting biomass (this included both microscopic and macroscopic characteristics) can help facilitate using the correct species (e.g., an authenticated voucher specimen was stored on file for species identification). An extract was obtained using hot water (between about 50° C. and about 100° C.) as a solvent. The extract is concentrated to a ratio of approximately 5:1. The extract is then dried. The extract is tested for a minimum of approximately 0.01% isoquercetrin via UV-Vis Spectrophotometry (isoquercetrin is used as reference substance). If the extract falls outside the desired standards above, it is titrated with a dried extract that had undergone the same process as above. The final extract dry concentrate appears as a yellow-brown colored powder.

In one embodiment, the *E. arvense* herb preparation is standardized to organic silicon content and flavonoid content (expressed as isoquercetrin) using the methods described above.

In some embodiments, it is *C. nurvala* and/or *L. aggregata*, and not *E. arvense*, that is standardized. In some other embodiments, all of the three are standardized. In some other embodiments, none of the three is standardized. For example, the herb-containing composition can comprise standardized *C. nurvala* and not standardized *E. arvense* and *L. aggregata*. Alternatively, the composition can comprise standardized *E. arvense* and not standardized *C. nurvala* and *L. aggregata*. Alternatively, the composition can comprise standardized *L. aggregata* and not standardized *C. nurvala* and *E. arvense*. In one embodiment, the composition can comprise standardized *C. nurvala* and *E. arvense* and not standardized *L. aggregata*. Alternatively, the composition can comprise standardized *C. nurvala* and *L. aggregata*, and not standardized *E. arvense*. Alternatively, the composition can comprise standardized *E. arvense* and *L. aggregata*, and not standardized *C. nurvala*. The standardization can be accomplished via any suitable compound, such as silicon, saponins, tannins, lupeol, etc. For example, the *Crateva nurvala* extract preparation can be standardized to have at least one of the following based on total weight of the *Crateva nurvala* root extract preparation: (i) saponins not less than 25%; (ii) tannins not less than 2%; and (iii) lupeol not less than 1.5%.

Other Constituents

The herb-containing compositions described herein can include constituents in addition to the herbal constituents *C. nurvala*, *E. arvense*, and *L. aggregata*. For example, in one embodiment, the composition can contain silicon, such as in the form of silica, such as anhydrous silica. The additional silicon assists with urogenital tissue support, strengthening and firmness. In one embodiment, the herb-containing composition contains from about 10 mg dry weight equivalents to about 71 mg dry weight equivalents of total silicon per oral dosage unit. In another embodiment, the herb-containing composition contains from about 15 mg dry weight equivalents to about 45 mg dry weight equivalents of total silicon per oral dosage unit. In another embodiment, the herb-containing composition contains from about 28 mg dry weight equivalents to about 34 mg dry weight equivalents of total silicon per oral dosage unit.

In another embodiment, the herb-containing composition contains phosphorus. In one embodiment, the herb-containing composition contains from about 5 mg dry weight equivalents of phosphorus to about 60 mg dry weight equivalents of phosphorus per oral dosage unit. In another embodiment, the herb-containing composition contains from about 10 mg dry weight equivalents of phosphorus to about 50 mg dry weight equivalents of phosphorus per oral dosage unit. In another embodiment, the herb-containing composition contains from about 20 mg dry weight equivalents of phosphorus to about 30 mg dry weight equivalents of phosphorus per oral dosage unit.

In another embodiment, the herb-containing composition contains calcium. In one embodiment, the herb-containing composition contains from about 1 mg dry weight equivalents of calcium to about 30 mg dry weight equivalents of calcium per oral dosage unit. In another embodiment, the herb-containing composition contains from about 5 mg dry weight equivalents of calcium to about 25 mg dry weight equivalents of calcium per oral dosage unit. In another embodiment, the herb-containing composition contains from about 10 mg dry weight equivalents of calcium to about 20 mg dry weight equivalents of calcium per oral dosage unit.

In another embodiment, the herb-containing composition contains magnesium. In one embodiment, the herb-containing composition contains from about 1 mg dry weight equivalents of magnesium to about 30 mg dry weight equivalents of magnesium per oral dosage unit. In another embodiment, the herb-containing composition contains from about 5 mg dry weight equivalents of magnesium to about 25 mg dry weight equivalents of magnesium per oral dosage unit. In another embodiment, the herb-containing composition contains from about 10 mg dry weight equivalents of magnesium to about 20 mg dry weight equivalents of magnesium per oral dosage unit.

The herb-containing composition can take any suitable form, depending on the application. For example, the composition can be a part of a cream. In one embodiment, the herb-containing composition contains from about 1 mg to about 100 mg dry weight equivalents *C. nurvala* stem/bark extract per gram of cream. In another embodiment, the herb-containing composition contains from about 10 mg to about 60 mg dry weight equivalents *C. nurvala* stem/bark extract per gram of cream. In another embodiment, the herb-containing composition contains from about 40 mg to about 60 mg dry weight equivalents *C. nurvala* stem/bark extract per gram of cream.

In another embodiment, the herb-containing composition contains from about 1 mg to about 60 mg dry weight equivalents *E. arvense* herb per gram of cream. In another embodiment, the herb-containing composition contains from about 5 mg to about 40 mg dry weight equivalents *E. arvense* herb per gram of cream. In another embodiment, the herb-containing composition contains from about 10 mg to about 30 mg dry weight equivalents *E. arvense* herb per gram of cream.

In one embodiment, the herb-containing composition contains orange oil. In one embodiment, the herb-containing composition contains from about 1 mg to about 30 mg orange oil per gram of cream. In another embodiment, the herb-containing composition contains from about 5 mg to about 25 mg dry orange oil per gram of cream. In another embodiment, the herb-containing composition contains from about 8 mg to about 12 mg orange oil per gram of cream.

In one embodiment, the herb-containing composition contains *Juniperus virginiana* (Cedarwood) stem essential oil. In one embodiment, the herb-containing composition contains from about 1 µg to about 1,000 µg *J. virginiana* stem essential oil per gram of cream. In another embodiment, the herb-containing composition contains from about from about 250 µg to about 750 µg *J. virginiana* stem essential oil per gram of cream. In another embodiment, the herb-containing composition contains from about 400 μg to about 600 μg *J. virginiana* stem essential oil per gram of cream.

In one embodiment, the herb-containing composition contains Myrrh oil. In one embodiment, the herb-containing composition contains from about 1 μg to about 1,000 μg Myrrh oil per gram of cream. In another embodiment, the herb-containing composition contains from about from about 250 μg to about 750 μg Myrrh oil per gram of cream. In another embodiment, the herb-containing composition contains from about 400 μg to about 600 μg Myrrh oil per gram of cream.

In one embodiment, the herb-containing composition contains Orange flower oil. In one embodiment, the herb-containing composition contains from about 1 μg to about 1,000 μg Orange flower oil per gram of cream. In another embodiment, the herb-containing composition contains from about from about 250 μg to about 750 μg Orange flower oil per gram of cream. In another embodiment, the herb-containing composition contains from about 400 μg to about 600 μg Orange flower oil per gram of cream.

In one embodiment, the herb-containing composition contains *Cupressus sempervirens* (Cypress) leaf oil. In one embodiment, the herb-containing composition contains from about 1 μg to about 1,000 μg *C. sempervirens* leaf oil per gram of cream. In another embodiment, the herb-containing composition contains from about from about 50 μg to about 500 μg *C. sempervirens* leaf oil per gram of cream. In another embodiment, the herb-containing composition contains from about 75 μg to about 125 μg *C. sempervirens* leaf oil per gram of cream.

In another embodiment, the herb-containing composition contains d-alpha-tocopheryl acetate (Natural Vitamin E). In one embodiment the herb-containing composition contains d-alpha-tocopheryl acetate. In one embodiment, the herb-containing composition contains from about 0.1 mg to about 25 mg d-alpha-tocopheryl acetate per gram of cream. In another embodiment, the herb-containing composition contains from about 1 mg to about 10 mg dry d-alpha-tocopheryl acetate per gram of cream. In another embodiment, the herb-containing composition contains from about 4 mg to about 6 mg d-alpha-tocopheryl acetate per gram of cream.

In another embodiment, the herb-containing composition contains diazolidinylurea. In one embodiment, the herb-containing composition contains diazolidinylurea. In one embodiment, the herb-containing composition contains from about 0.1 mg to about 10 mg diazolidinylurea per gram of cream. In another embodiment, the herb-containing composition contains from about 1 mg to about 5 mg dry diazolidinylurea per gram of cream. In another embodiment, the herb-containing composition contains from about 3 mg to about 3.5 mg diazolidinylurea per gram of cream.

In another embodiment, the herb-containing composition contains hydroxybenzoates. In one embodiment, the herb-containing composition contains hydroxybenzoates. In one embodiment, the herb-containing composition contains from about 0.1 mg to about 5 mg hydroxybenzoates per gram of cream. In another embodiment, the herb-containing composition contains from about 0.5 mg to about 3 mg dry hydroxybenzoates per gram of cream. In another embodiment, the herb-containing composition contains from about 1 mg to about 2 mg hydroxybenzoates per gram of cream.

In another embodiment, the herb-containing composition contains extracts of *C. nurvala* stem/bark; *E. arvense* leaf/stem; and *L. aggregata* root; Orange oil; *J. virginiana* stem; Myrrh oil; Orange flower oil; *C. sempervirens* leaf; d-alpha-tocopheryl acetate; diazolidinylurea; and hydroxybenzoates.

Medicinal Properties and Uses of Compositions

One embodiment provides herb-containing compositions useful in a method of prophylaxis or treatment of disorders of the urogenital system, e.g., urinary incontinence, enuresis (e.g., bed-wetting), benign prostatic hyperplasia, overactive bladder, nocturia, urinary calculi, cystitis, and UTIs. Not to be bound by any particular theory, but in some embodiments the primary active ingredients present in both the *Crateva* and *Equisetum* are the saponins and plant sterols. *Crateva* contains flavonoids, glucosinolates and the plant sterol, lupeol, while *Equisetum* contains the mineral, silica, flavonoids (isoquercetin, luteolin, and kaempferol) and the saponin, equisetin. Nadkarni K. M. et al., Indian Materia. Medica. Bombay Popular Prakashan; British Herbal Pharmacopeia. Publ: British Herbal Medicine Association 1983; Bone K. *Clinical Applications of Ayurvedic and Chinese Herbs. Monographs for the western herbal practitioner.* Phytotherapy Press, Warwick, Qld, Australia 1997; The German Commission E Monographs, 1998; D'Agostino M. et al., Boll. Soc. Ital. Biol. Sper., 30; 60(12):2241-5 (1984); Pengelly A. *The constituents of medicinal plants: an introduction to the chemistry and therapeutics of herbal medicine*. Sunflower Herbal $2^{nd}$ Edition, Merriwa, NSW, Australia, 1996; Lakshmi V. et al., Planta Medica, 32: 214-216 (1977).

In one embodiment, the herb-containing compositions can be useful in the prevention and treatment of urinary calculi. *Crateva* and *Equisetum* have been shown to alter urinary electrolytes in such a way so as to reduce lithogenic potentiality. Varalakshmi P et al., J. Ethnopharmacology, 28: 313-321 (1990); Anand R. et al., Indian J. Pharmacology, 27: 265-268 (1995); Grases F. et al., Int. Urol. Nephrol., 26(5): 507-511 (1994). *Crateva* has also been found to inhibit small intestinal Na-K-ATPase. Varalakshmi P. et al., J. Ethnopharmacology, 31: 67-73 (1991). These effects may be due primarily to the presence of the sterol lupeol. A number of studies have shown that lupeol has anti-oxaluric and anti-calcuric effects leading to increased spontaneous passing of stones and symptomatic relief. Varalakshmi P et al., J. Ethnopharmacology, 28: 313-321 (1990); Anand R. et al., Indian J. Pharmacology, 27: 265-268 (1995); Malini M. M., et al., Jpn. J. Med. Sci. Biol., 48(5-6):211-20 (1995); Lakshmi V. et al., Planta Medica, 32: 214-216 (1977).

In one embodiment, it is hypothesized that this passage of the stone may be produced via a tonic contractile action of the drug on the smooth muscle. Varalakshmi P et al., J. Ethnopharmacology, 28: 313-321 (1990); Anand R. et al., Indian J. Pharmacology, 27: 265-268 (1995); Deshpande P. J. et al., Indian J. Med. Res., 76(Suppl): 46-53 (1982). *Equisetum* may also assist with incontinence via a similar mechanism. Kaempferol, luteolin and isoquercetin, found in *Equisetum* are documented to inhibit xanthine oxidase and subsequent urate calculi formation. Nagao A. et al., Biosci. Biotechnol. Biochem., 63(10):1787-90 (1999). These herbal drugs can act to improve the tone of the bladder wall. In 1982, Deshpande et al. reported that *Crateva* has beneficial effects on neurogenic bladder and post-prostatectomic atony of the bladder. Deshpande P. J. et al., Indian J. Med. Res., 76(Suppl):46-53 (1982).

In one embodiment, the herb-containing compositions can be useful in the prevention and treatment of incontinence and benign prostatic hypertrophy and urinary incontinence. *Crateva* administration produces a marked relief of symptoms of frequency, incontinence, pain and retention of urine in men with hypotonic bladder as a result of benign prostatic hypertrophy. Deshpande P. J. et al., Indian J. Med. Res., 76 (Suppl):46-53 (1982). *Crateva* can act to increase the tone of the bladder and the expulsive force of urine, thereby helping effective evacuation. Deshpande P. J. et al., Indian J. Med. Res., 76 (Suppl):46-53 (1982)—cystometric studies analyzed in this paper also show that *Crateva* normalizes the tone of the urinary bladder and significantly decreases residual urine volume. The herb-containing compositions provided herein, therefore, are useful in the prevention and treatment of urinary incontinence.

These results are also supported by animal studies where *Crateva* has been shown to increase the tone of both smooth and skeletal muscle in vitro. Das P. K. et al., J. Res. Ind. Med., 9:49 (1974). Animal studies show that 40 days of treatment with *Crateva* resulted in hypertonic curves of the urinary bladder when compared to initial curves. Das P. K. et al., J. Res. Ind. Med., 9:49 (1974).

*Equisetum* is rich in silicic acid and silicates. In one embodiment, silica supports the regeneration of connective tissue. Chevallier, A., *The Encyclopedia of Medicinal Plants*, (Horn V. and Weil, C., Eds.) Dorling Kindersley Ltd., London (1996). Thus, the herb-containing compositions described herein can be useful in the prophylaxis or treatment of disorders of the urogenital system, for example, urinary incontinence, enuresis (e.g., bed-wetting), benign prostatic hyperplasia, urinary calculi, cystitis, and UTIs.

The herb-containing compositions provided herein are useful in the prevention and treatment of UTIs and cystitis. It has been shown in rat studies that some species of the *Equisetum* family have a diuretic action, shown by excretion of sodium, potassium and chloride, similar to that of other drugs such as hydrochlorothiazide. Perez Gutierrez R. M. et al., J. Ethnopharmacol., 14(2-3):269-272 (1985); D'Agostino M. et al., Boll. Soc. Ital. Biol. Sper., 60(12): 2241-5 (1984). A more recent study using rats also demonstrated beneficial affects of the drugs in urolithiasis. Grases F. et al., Int. Urol. Nephrol., 26(5):507-511 (1994). These authors suggest that this result could be due to the antibacterial action of the constituents, namely, the saponins. Interestingly, *Crateva* has anti-inflammatory and antibacterial properties. Nadkarni K. M. et al., Indian Materia Medica. Bombay Popular Prakashan; Bone K. *Clinical Applications of Ayurvedic and Chinese Herbs. Monographs for the western herbal practitioner*. Phytotherapy Press, Warwick, Qld, Australia 1997; Salvat A. et al., Lett. Appl. Microbiology, 32(5): 293-7 (2001); Xu H X et al., Phytother. Res., 15(1): 39-43 (2001); Geetha T. et al., Gen. Pharmacol., 32(4):495-7 (1999); Geetha T. et al., J. Ethnopharmacol., 76(1):77-80 (2001). Combined with *Crateva*'s tonic effects on smooth muscle, it is considered to assist with bladder evacuation, thereby decreasing residual urine, a known to contributing factor to UTIs. Deshpande P. J. et al., Indian J. Med. Res., 76(Suppl):46-53 (1982).

Isoquercetin, found in *Equisetum*, is known to have anti-inflammatory effects via inhibition of inflammatory prostaglandins, although *Crateva* is thought to produce anti-inflammatory effects via a different mechanism. D'Agostino M. et al., Boll. Soc. Ital. Biol. Sper., 30; 60(12):2241-5 (1984); Geetha T. et al., Gen. Pharmacol., 32(4):495-7 (1999). The positive effect on chronic urinary tract infections is most likely a combination of anti-bacterial and anti-inflammatory actions.

In one embodiment, the herb-containing compositions can be useful in the prevention and treatment of urinary incontinence, UTIs, and enuresis. There is evidence for the use of Virginia cedarwood in treating incontinence, enuresis and assisting bladder tone as well as bladder infections, difficult urination and cystitis. Tisserand and Balacs, *Essential Oil Safety. A Guide for Health Care Professionals*. Churchill Livingstone, U. K., 1995; 28-29, 31, 33-34; Price, S. *Practical Aromatherapy*. Thorsons, Harper Collins Publishers, California, U.S., 1983; 157-8, 170-171, 174, 185; Davis, P. *Aromatherapy An A-Z*. The C. W. Daniel Company, Essex, England, 1998; 194; Valnet, J. *The Practice of Aromatherapy*. Saffron Walden, The C. W. Daniel Company, Essex, England, 1980; 120-121; Price, S. *The Aromatherapy Workbook*. Thorsons (Harper Collins), California, USA, 1993; 67; Caddy, R., *Aromatherapy Essential Oils in Colour*. Amberwood Publishing Ltd, East Horsley, Surrey, England, 1997; 14. The documented properties likely to produce this effect include the antispasmodic, diuretic, antiseptic and astringent.

Cypress is documented as an antispasmodic, astringent, antiseptic, deodorant, diuretic and tonic that may promote venous circulation to the kidneys and bladder area, improve bladder tone and assist with urinary incontinence and enuresis. Tisserand and Balacs, *Essential Oil Safety. A Guide for Health Care Professionals*. Churchill Livingstone, U. K., 1995; 28-29, 31, 33-34; Valnet, J. *The Practice of Aromatherapy*. Saffron Walden, The C. W. Daniel Company, Essex, England, 1980; 120-121, Holmes, P. *The Energetics of Western Herbs*. Artemis Press, Boulder, Colo., USA, 1989; 567-569, 792; Damian, P & K. *Aromatherapy Scent and Psyche*. Healing Arts Press, Rochester, Vt., Canada, 1995; 187-188; Price, S. *The Aromatherapy Workbook*. Thorsons (Harper Collins), California, USA, 1993; 67; Chidell, L. *Aromatherapy. A Definitive Guide to Essential Oils*. Hodder and Stoughton Ltd, Kent, U K, 1992; 23-24, 80-81; Keller, E. *The Compete Home Guide to Aromatherapy*. H J Kramer, Inc, Tiburon, Calif., USA, 1991; 178-179.

Recent literature describes Myrrh as an astringent and antiseptic that produces a soothing effect on mucous membranes of the urinary system and promotes healing of tissues. Battaglia, S. *The Complete Guide to Aromatherapy*. The Perfect Portion Pty Ltd, Virginia, Brisbane, Qld, Australia, 1995; 110-113, 116, 150-151, 158-159, 182-183, 184-185, 187; Lawless, J. *The Encyclopaedia of Essential Oils*. (1992) Element Books for Jacaranda Wiley, Ltd, Australia, 1992; 76-77, 88-89, 135-136. Orange and Neroli are documented as having antispasmodic, antiseptic and deodorant effects. 6,10; Sheppard-Hanger. *The Aromatherapy Practitioner Manual*. Aquarius Publishing, Willetton, Western Australia, 1995; 183; Sellar, W. *The Directory of Essential Oils*. Saffron Walden, The C.W. Daniel Company, Essex, England, 1992; 50-51, 106-107; Keller, E. *The Compete Home Guide to Aromatherapy*. H J Kramer, Inc, Tiburon, Calif., USA, 1991; 178-179.

In one embodiment, the herb-containing compositions can be useful in the prevention and treatment of disorders of the prostate, e.g., benign prostatic hyperplasia. Essential oils are also recommended for male reproductive health, indicating a possible effect on the prostate in men. Battaglia, S. *The Complete Guide to Aromatherapy*. The Perfect Portion Pty Ltd, Virginia, Brisbane, Qld, Australia, 1995; 110-113, 116, 150-151, 158-159, 182-183, 184-185, 187; Price, S. *Practical Aromatherapy*. Thorsons, Harper Collins Publishers, California, U.S., 1983; 157-8, 170-171, 174, 185; Lawless, J. *The Encyclopaedia of Essential Oils*. (1992) Element Books for Jacaranda Wiley, Ltd, Australia, 1992; 76-77, 88-89, 135-136; Valnet, J. *The Practice of Aromatherapy*. Saffron Walden, The C. W. Daniel Company, Essex, England, 1980; 120-121.

Certain drugs commonly prescribed for urinary incontinence, such as oxybutynin hydrochloride, inhibit the muscarinic action of acetylcholine on smooth muscle, producing a direct antispasmodic action; that is, they relax the detrusor muscle. Tapp A. J. S. et al., Brit. J. Obstetrics and Gynecology; 97: 521-6 (1990). This antispasmodic effect is preferred to the anticholinergic effect of drugs previously used for patients with urinary incontinence. The antispasmodic effect of these essential oils, whilst not provided in more specific detail, may also be producing an action similar to currently prescribed drug medications.

Herbal diuretics are documented as increasing blood flow through the kidneys without resorption at the distal tubule of the nephron and associated loss of electrolytes (apart from potassium), as is the case with more sophisticated modern drug diuretics. Mills and Bone, *Principles and Practice of Phytotherapy*. Churchill Livingstone, 2000; 35, 220-222. Also, diuresis often does not result from herbal diuretic use. Mills and Bone, *Principles and Practice of Phytotherapy*. Churchill Livingstone, 2000; 35, 220-222. Not to be bound by any particular theory, but it may be that these herbal essential oils largely stimulate the blood flow to the kidneys resulting in an increase or greater efficiency in the production of urine. This effect, when combined with complete emptying of the bladder when voiding, may minimize the volume of urine lost through continual leakage.

Pharmaceutical Compositions and Formulations

One embodiment provides methods of preventing and/or treating a urogenital system disorder in a subject by administering to the subject an herb-containing composition in an amount sufficient to prevent or treat the urogenital system disorder (i.e., pharmaceutically effective amount). The composition can be any of the compositions described herein. A subject in need of the presently described composition (and the administration thereof) can be one suffering any of the urogenital system disorders, including at least one of (i) urinary incontinence and (ii) overactive bladder symptoms. For example, the urogenital system disorder can include urinary incontinence, enuresis, benign prostatic hyperplasia, nocturia, urinary calculi, cystitis, OAB, a urinary tract infection, and the like.

In one embodiment, the herb-containing compositions can be used alone or further formulated with pharmaceutically acceptable compositions, vehicles, or adjuvants with a favorable delivery profile (i.e., suitable for delivery to a subject, particularly one in need thereof). Such compositions typically comprise the herb-containing composition and a pharmaceutically acceptable carrier. "Pharmaceutically acceptable carrier" in some embodiments is intended to include any and all solvents, dispersion media, coatings, antibacterial and antifungal compositions, isotonic and absorption delaying compositions, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. The use of such media and compositions for pharmaceutically active substances is well known in the art. Except insofar as any conventional media or composition is incompatible with the active composition, use thereof in the compositions is contemplated. Supplementary active compositions can also be incorporated into the compositions.

A pharmaceutical composition is formulated to be compatible with its intended route of administration. Examples of routes of administration include, e.g., oral; transdermal (i.e., topical), and transmucosal administration. The pH can be adjusted with acids or bases, such as hydrochloric acid or sodium hydroxide.

Oral compositions generally include an inert diluent or an edible carrier. They can be enclosed in gelatin capsules, caplets or compressed into tablets. For the purpose of oral therapeutic administration, the herb-containing composition can be incorporated with excipients and used in the form of tablets, troches, or capsules. Oral compositions can also be prepared using a fluid carrier for use as a mouthwash, wherein the composition in the fluid carrier is applied orally and swished and expectorated or swallowed. Pharmaceutically compatible binding compositions, and/or adjuvant materials can be included as part of the composition. The tablets, pills, capsules, troches and the like can contain any of the following ingredients, or compositions of a similar nature: a binder such as microcrystalline cellulose, gum tragacanth or gelatin; an excipient such as starch or lactose, a disintegrating composition such as alginic acid, Primogel, or corn starch; a lubricant such as magnesium stearate or Sterotes; a glidant such as colloidal silicon dioxide; a sweetening composition such as sucrose or saccharin; or a flavoring composition such as peppermint, methyl salicylate, or orange flavoring. The herb-containing compositions provided herein can also be formulated as a topical cream for transdermal or transmucosal administration.

In one embodiment, the herb-containing compositions are prepared with carriers that will protect the composition against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

The pharmaceutical compositions can be included in a container, pack, or dispenser together with instructions for administration.

As a result of administrating the presently described herb-containing composition to a subject in need thereof, the symptoms in the subject can be alleviated. For example, the treatment can result in a reduction in at least one of (i) urinary incontinence and (ii) OAB. In one embodiment, the treatment can result in an improvement of at least one of average daily frequency of urination; average nightly frequency of urination; total urinary incontinence episodes; stress incontinence episodes; and urinary urgency episodes.

In contrast to some of the pre-existing herb-containing compositions, the compositions provided herein surprisingly can provide efficacy and efficiency much higher that the pre-existing compositions. For example, the compositions provided herein can result in improvement that is about at least two times, such as at least three times, four times, five times, or more, as fast as the pre-existing herb-containing compositions. For example, compared to the composition as provided in U.S. Pat. No. 7,378,115, which achieved improvement in about 3 months, the compositions provided herein can achieve a comparable level of improvement in less than three months, such as less than two months, such as less than one month, such as less than 2 weeks. In one embodiment, the presently described composition can accomplish the improvement between about two weeks and about two months, such as about two weeks, or such as about one month.

The articles "a" and "an" are used herein to refer to one or to more than one (i.e., to at least one) of the grammatical object of the article. By way of example, "a polymer resin" means one polymer resin or more than one polymer resin. Any ranges cited herein are inclusive. The terms "substantially" and "about" used throughout this Specification are used to describe and account for small fluctuations. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

REFERENCES

1. Desphande P. J, Sahu M, Kumar P, 1982. *Crateva nurvala* Hook and Forst (Varuna) the Ayurvedic drug of choice in urinary disorders. *Indian Journal of Medical Research;* 76 (Suppl) December: 46-53.
2. Anand R, Patnaik G K, Kamal Roy, Bhaduri A P, 1995. Antioxaluric and anticalciuric activity of lupeol derivatives. *Indian Journal of Pharmacology;* 27: 265-268.
3. Grases F, Melero G. Costa-Bauza A, Prieto R, March J G, 1994. Urolithiasis and phytotherapy. *International Journal of Urology and Nephrology;* 26(5): 507-511.
4. Varalakshmi P, Shamila Y, Latha E. Effect of *Crateva nurvala* in experimental urolithiasis. J Ethnopharmacology 1990; 28: 313-321.
5. Malini M M, Baskar R, Varalakshmi P. Effect of lupeol, a pentacyclic triterpene, on urinary enzymes in hyperoxaluric rats. Jpn J Med Sci Biol 1995 October-December; 48(5-6): 211-20.
6. Das P K, Rathor R S, Lal R, Tripathi R M, Ram A K, Biswas M, 1974. Anti-inflammatory and anti-arthritic activity of Varuna. *Journal of Research of Indian Medicine;* 9:49.
7. Nagao A, Seki M, Kobayashi H, 1999. Inhibition of xanthine oxidase by flavonoids. Biosci *Biotechnology Biochemistry;* 63(10): 1787-90.
8. Steels E, Ryan J, Seipel T, Rao A, 2002. *Crateva* and *Equisetum* reduce urinary incontinence symptoms. *Australian Continence Journal;* 8 (3).
9. Schauss A G, Spiller G, Chaves S, Gawlicka A, 2006. Reducing the symptoms of overactive bladder and urinary incontinence: results of a two-month, double-blind, placebo-controlled clinical trial. Poster presentation FASEB, San Francisco, April, 2006.
10. Robinson D, Pearce K F, Preisser J S, Dugan E, Suggs P K and Cohen S J, 1998. Relationship between patient reports of urinary incontinence symptoms and quality of life measures. Obstetrics and Gynaecology; 91 (2): 224-228.
11. Coyne K, Payne C, Bhattacharyya S, Revicki D, Thompson C, Corey R, Hunt T, 2004. The impact of urinary urgency and frequency on health-related quality of life in overactive bladder: Results from a national community survey. *Value in Health;* 7(4).
12. Bone K. Clinical Applications of Ayurvedic and Chinese Herbs, 1997. *Monographs for the western herbal practitioner.* Phytotherapy Press, Warwick, Queensland, Australia.
13. Geetha T, Varalakshmi P, 2001. Anti-inflammatory activity of lupeol and lupeol linoleate in rats. *Journal of Ethnopharmacology;* 76(1): 77-80.
14. Geetha T, Varalakshmi P, 1999. Anticomplement activity of triterpenes from *Crateva nurvala* stem bark in adjuvant arthritis in rats. *General Pharmacology;* 32(4):495-7.
15. Chan Wang, Yue Dai, Jian Yang, Guixin Chou, Changhong Wang, Zhengtao Wang, 2007. Treatment with total alkaloids from Radix Linderae reduces inflammation and joint destruction in type II collagen-induced model for rheumatoid arthritis. *Journal of Ethnopharmacology;* 111: 322-328.
16. Yubin Luo, Mei Liu, Xiujuan Yao, Yufeng Xia, Yue Dal, Guixin Chou and Zhengtao Wang, 2009. Total alkaloids from Radix Linderae prevent the production of inflammatory mediators in lipopolysaccharide-stimulated RAW 264.7 cells by suppressing NF-κB and MAPKs activation. *Cytokine;* 46(1): 104-110.
17. Qinglin L, Guixin C, Changgui D, Zhengtao W, Fang H, 1997-12. Studies on the analgesic and anti-inflammatory action of radix Linderae extract. *Journal of Chinese Medicinal Materials.* (China Pharmaceutical University, Nanjing 210038) (Abstract).
18. Runwei Yan, Yang Yang, Yingying Zeng, Guolin Zou, 2009. Cytotoxicity and antibacterial activity of *Lindera strychnifolia* essential oils and extracts. *Journal of Ethnopharmacology;* 121: 451-455.
19. Nagaraj M, Sunitha S, Varalakshmi P, 2000. Effect of lupeol, a pentacyclic triterpene, on the lipid peroxidation and antioxidant status in rat kidney after chronic cadmium exposure. *Journal of Applied Toxicology;* 20(5): 413-417.
20. Ohno T, Takemura G, Murata I, Kagawa T, Akao S, Minatoguchi S, Fujiwara T and Fujiwara H, 2005. Water extract of the root of *Lindera strychnifolia* slows down the progression of diabetic nephropathy in db/db mice. *Life Sciences;* 77(12):1391-1403.
21. Bensky D and Gamble A, 1993. Chinese Herbal Materia Medica, Revised Edition. England Press, Seattle, Wash., USA.
22. Shimomura M, Ushikoshi H, Hattori A, Murata I, Ohno Y, Aoyama T, Kawasaki M, Nishigaki K, Takemura G, Fujiwara T, Fujiwara H, Minatoguchi S, 2010. Treatment with *Lindera strychnifolia* reduces blood pressure by decreasing sympathetic nerve activity in spontaneously hypertensive rats. *American Journal of Chinese Medicine;* 38(3): 561-8.
23. Noda Y, Mori A, Anzai K, Packer L, 1999. Superoxide anion radical scavenging activity of Uyaka (*Lindera strychnifolia*), a natural extract used in traditional medicine. Antioxidant Food Supplements in Human Health.
24. Bin Li, Gil-Saeng Jeong, Dae-Gill Kang, Ho-Sub Lee and Youn-Chul Kim, 2009. Cytoprotective effects of lindenenyl acetate isolated from *Lindera strychnifolia* on mouse hippocampal HT22 cells. *European Journal of Pharmacology.* Neuropharmacology and Analgesia; 16(1-3): 58-65.

The invention is further defined by reference to the following examples, which are not meant to limit the scope of the present invention. It will be apparent to those skilled in the art that many modifications, both to the materials and methods, may be practiced without departing from the purpose and interest of the invention.

NON-LIMITING WORKING EXAMPLES

Example 1

Clinical Trial of Herb-Containing Natural Therapeutic Combination for Urinary Incontinence and OAB (Overactive Bladder) Symptoms General Studies were conducted to investigate the effectiveness of an herb-containing natural therapeutic bladder control preparation in relieving urinary incontinence and OAB (overactive bladder) symptoms (hereinafter, "UI/OAB bladder control preparation"). The interviews were conducted at Kelvin Grove Natural Medicine clinic, Brisbane, Australia.

Materials and Methods

Test Preparation

The herbal components of bladder control preparation are listed on the ARTG (Australian Register of Therapeutic Goods) as safe for use. Each preparation contained the herbs, C. nurvala stem/bark extract, E. arvense stem extract and L. aggregata root extract. For example, each tablet contained dry weight equivalents as follows: C. nurvala stem/bark extract (3,000 mg) 3 g, E. arvense (Horsetail) herb (1,500 mg) 1.5 g, and L. aggregata (Lindera) root ((1,500 mg) 1.5 g.

Study Design

Nine (9) adults experiencing symptoms of urge incontinence and/or stress incontinence, OAB, urinary urgency, nocturia or urinary frequency on a regular basis were recruited through Kelvin Grove Natural Medicine clinic and advertisements in local health food stores. One participant did not complete the study due to unrelated reasons. There were eight (8) participants (one male and seven females) completing the study with an average age of 58 years (range 45-80 years).

All participants met the following criteria:
  had not undergone recent surgery particularly hysterectomy or prolapse repair within the last 12 months,
  did not have any serious health conditions such as diabetes mellitus, heart disease, pancreatic disease, hepatic disease or chronic inflammatory conditions,
  were not currently being treated for psychotic disturbances, and
  did not use any medicine for incontinence symptoms in the last month prior to commencement of the study.

None of the participants were engaging in the specific pelvic exercises to improve muscle tone prior to the study.

The treatment protocol consisted of ingesting once daily, a prescribed herbal blend equivalent to dry extracts of 6 g C. nurvala, 3 g E. arvense, and 3 g L. aggregata daily over a period of two months. Average daily and nightly (nocturia) frequency of urination, total urinary incontinence episodes, stress incontinence episodes and urinary urgency episodes were assessed, compared to baseline, at 2 weeks, one month, and again at two months. These results were compared using a paired t-test.

Efficacy of treatment was also assessed, compared to baseline and one month by using the short versions of the Incontinence Impact Questionnaire (IIQ) and the Urogenital Distress Inventory (UDI). The short version (six questions) of the IIQ assesses the impact of incontinence on daily activities, such as household chores, physical activity and social activities. The questions in the UDI relate specifically to the physical aspects of incontinence and bladder control as detailed below in Table 3.

TABLE 3

| Urogenital Distress Inventory |
|---|
| Do you experience, and if so, how much are you bothered by: |
| Frequent urination |
| Leakage due to feeling or urgency |
| Leakage due to activity, coughing, sneezing |
| Small amounts of leakage (drops) |
| Difficulty emptying bladder |
| Pain or discomfort in lower abdominal or genital area |

The short version (six questions) of the IIQ assesses the impact of incontinence on daily activities, such as household chores, physical activity and social activities as summarized below in Table 4.

TABLE 4

| Incontinence impact questionnaire |
|---|
| Has urine leakage affected the following: |
| Household chores |
| Physical recreation |
| Entertainment activities |
| Travel >30 min from home |
| Social activities |
| Emotional health |
| Feeling frustrated |

All questions were rated on a scale of 0 to 3 (0=not bothered, 1=slightly bothered, 2=moderately bothered, 3=extremely bothered). Both questionnaires were standardized disease specific questionnaires used to detect bothersome incontinence in older people. Robinson, D. et al., Obstetrics and Gynecology, 91:2, 224-8 (1998).

A positive improvement was defined as a statistically significant difference, i.e., p-value≤0.05, in a parameter measuring the physical aspects of incontinence or the physical or social activities of test subjects receiving the UI/OAB bladder control preparation when compared to the same parameter in human test subjects prior to receiving the UI/OAB bladder control preparation. A positive improvement in any parameter relating to the physical aspects of incontinence or overactive bladder or the physical or social activities of human test subjects receiving UI/OAB bladder control preparation when compared to the same parameter in human test subjects prior to receiving the bladder control test preparation demonstrates that the UI/OAB bladder control preparation is useful to prevent or treat a urogenital system disorder in a human subject, e.g., urinary incontinence; overactive bladder; enuresis; benign prostatic hyperplasia; nocturia; urinary calculi; cystitis; and urinary tract infection.

Results and Discussion

Frequency of Urination During the Day

The results demonstrated that the average frequency of urination during the day reduced significantly (p<0.005) during the two months of treatment. The number of times participants needed to empty the bladder reduced from an average of 12.4 (prior to treatment), to 9.8 times per day (after 2 weeks), 8 times per day (after one month), which is within the normal range, and 7.6 times per day (after two months).

Frequency of Nocturia

The results demonstrated that this treatment was effective in reducing the number of times participants needed to empty the bladder at night. There was a reduction in awakenings from 2.75 times per night initially to 0.625 times and 0.375 times and 0.313 times per night at two weeks and month 1 and month 2 respectively (all p values<0.05). Many of the participants were able to sleep though the night altogether after two weeks of treatment. In addition some participants commented that if they awoke with the need to urinate, they could hold the urine and return to sleep without having to get out of bed and without accident.

Urinary Urgency

The results demonstrated that urinary urgency reduced from an average of 3.75 times a day to 2.5 times (p<0.05) at week 2 and 1.4 times (p<0.05) at month 1 and 1.25 times (p<0.05) at month 2.

Urinary Incontinence

The results demonstrated that this treatment was effective in reducing the number of times participants experienced urinary incontinence. There was a reduction in incontinence episodes from 2 times per day initially to 0.5 times at 2 weeks and 0 times at month 1 and month 2 (p<0.05). A 50% reduction in pad by month one usage was also seen; however, at the month 1 stage some participants still elected to use a pad as a precautionary measure. By month 2 only one participant was still using pads.

The Urogenital Distress Inventory

Figure 2:
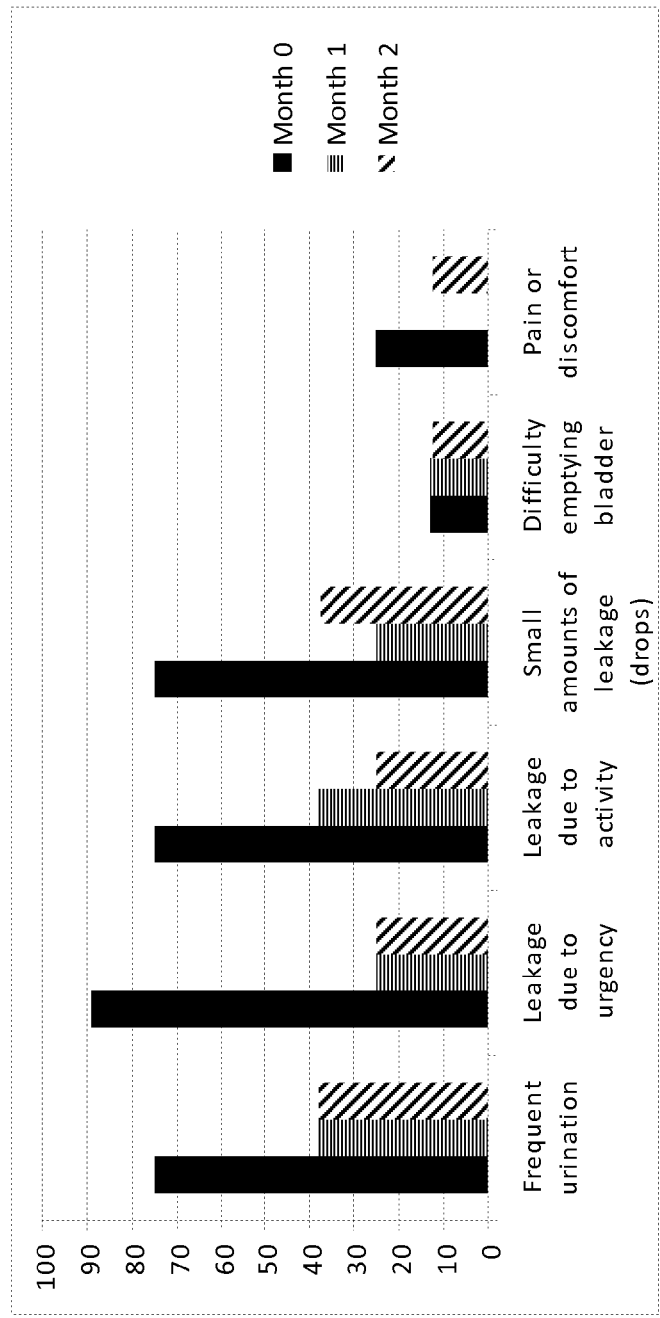
FIG. 2 is a histogram graph showing the percentage (%) of participant population experiencing symptoms of urinary incontinence and overactive bladder during clinical assessment in one embodiment.
Figure 3:
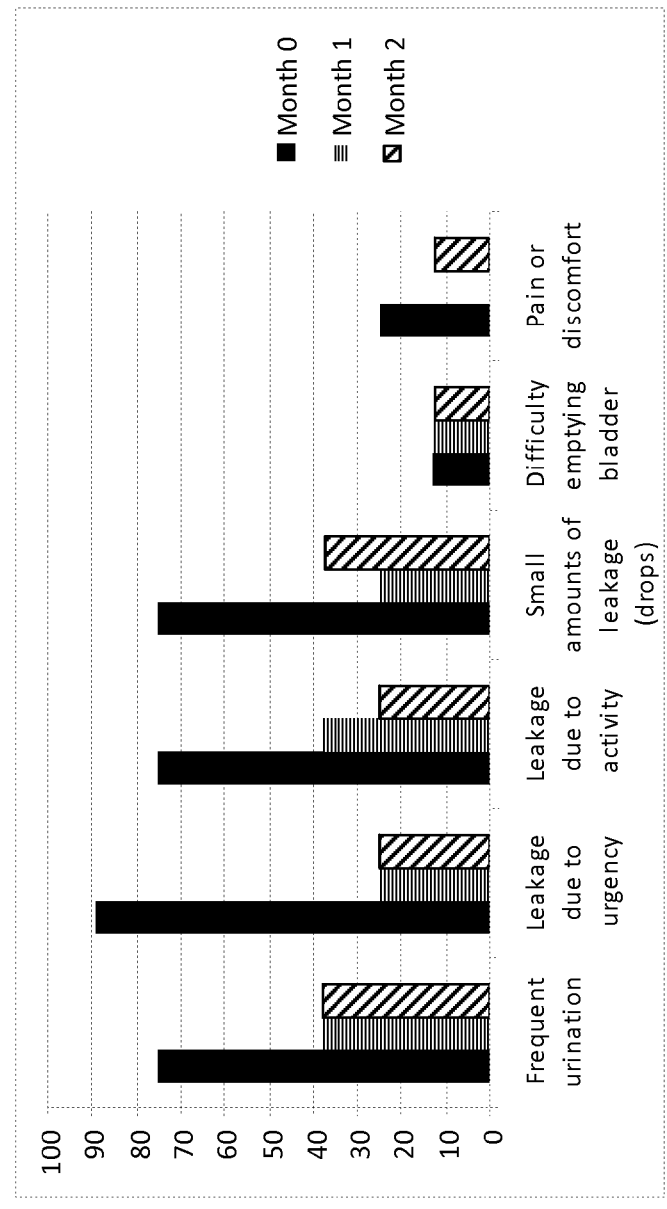
FIG. 3 is a histogram graph showing UDI Average Bothered Rating for symptoms during clinical assessment in one embodiment.

At baseline, symptoms experienced by most participants and causing bother (FIGS. 1 and 2) were: leakage due to urgency (88%), frequent urination (75%), leakage due to activity (75%), small amounts of leakage (75%) urinary incontinence (75%) and nocturia (63%). The average bothered rating results show (FIG. 3) that all symptoms were reduced by one month of treatment. There was a significant positive change after one month of treatment, which continued at month 2 for frequent urination (p=0.007; 0.005), leakage due to urgency (p=0.003; 0.002) and leakage due to activity (p=0.007; 0.005). The average bothered rating for small amounts of leakage was positive at month 1 and 2 (p=0.007; 0.003). The small regression in response seen at month 2 is likely due to the changed activities during month 2 including increased driving for long periods and camping in the rain.

The results of the questionnaire were analyzed using the paired t-test. There was a significant positive change after one month of treatment for frequent urination (p=0.007), leakage due to urgency (p=0.003), leakage due to activity (p=0.007), and small amounts of leakage (p=0.007).

Incontinence Impact Questionnaire

The activities that showed to be most impacted on by incontinence and OAB (FIG. 4) were: physical recreation, travel greater than 30 minutes from home and feeling frustrated, which were experienced by 63% of participants.

Figure 4:
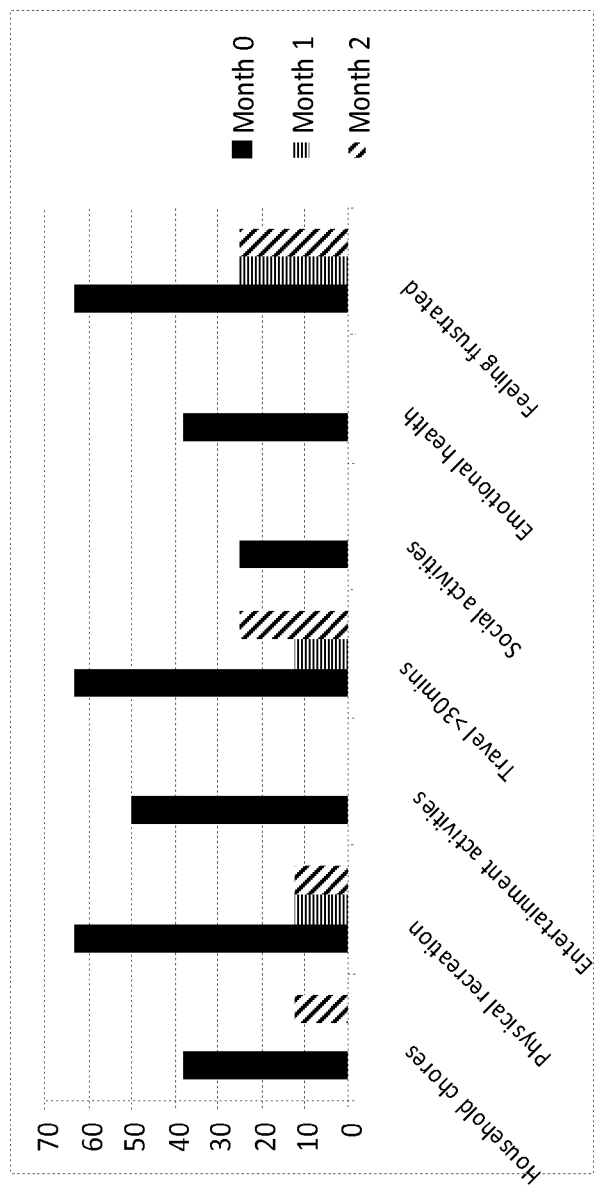
FIG. 4 is a histogram graph showing the percentage (%) of participant population experiencing symptoms IIQ during clinical assessment in one embodiment.

The results of the questionnaire were analyzed using the paired t-test (Table 5 and FIG. 4). The results clearly show that Quality of Life (assessed through difficulty in doing daily and social activities as well as emotional health and feelings of frustration) are adversely affected by having the symptoms of incontinence. By month one there was an improvement in the perception of the effect of incontinence on lifestyle and social activities, which continued to month 2 indicated by positive changes in response to all questions, including the most bothersome responses; physical recreation (p=0.014; 0.014), travel greater than 30 minutes from home (p=0.007; 0.009) and feeling frustrated (p=0.013; 0.013).

TABLE 5

Results of paired t-test (p-values) Urinary Distress Inventory and Incontinence Impact Questionnaire Urinary Distress Inventory

| T-test results | Frequent Urination | Leakage due to urgency | Leakage related to activity | Small amounts of leakage (drops) | Difficulty emptying bladder | Pain or discomfort |
|---|---|---|---|---|---|---|
| 0 vs. 1 month | * | * | * | * | Not significant | Not significant |
| 0 vs. 2 months | * | * | * | * | Not significant | Not significant |

Incontinence Impact Questionnaire

| T-test results | Household chores | Physical recreation | Entertainment activities | Travel greater than 30 min from home | Social activities | Emotional health | Feeling frustrated |
|---|---|---|---|---|---|---|---|
| 0 vs. 1 month | * | * | * | * | Not significant | * | * |
| 0 vs. 2 months | * | * | * | * | Not significant | * | * |

* = p values < 0.05

Participants were also asked, at the month 1 interview, if the treatment had improved their Quality of Life. Overall, 88% reported an improvement in QOL, at month 2 this increased to 100%. These results clearly indicate that there is a significant improvement in QOL for participants that experience relief or a reduction in the severity in the symptoms of urinary incontinence and OAB, including frequency, nocturia, urgency and bladder discomfort.

Effectiveness of Other Urinary Incontinence and Overactive Bladder Therapeutics

Earlier studies show that treatment with *Crateva* relieves incontinence, pain and retention of urine in men and that *Crateva* and Horsetail combined improves symptoms of urinary incontinence and quality of life. Deshpande P. J. et al., Indian J. Med. Res., 76 (Suppl):46-53 (1982); Steels et al, ACJ (2002); Schauss et al, FASEB (2006).

Commonly prescribed drug medications for UI and OAB e.g., oxybutynin hydrochloride, primarily act to inhibit the muscarinic action of acetylcholine on the smooth muscle of the bladder producing a direct antispasmodic action to relax the detrusor muscle. Wada Y. et al., Arch. Int. Pharmacodyn. Ther., 330(1):76-89 (1995); Tapp A. J. S. et al., Brit. J. Obstetrics Gynecology, 97: 521-6 (1990). These medications also produce unwanted anticholinergic effects, such as dry mouth, blurred vision and constipation. Pathak A S, Aboseif S R. Overactive Bladder: Drug therapy versus nerve stimulation. Nat Clin Pract Urol, 2(7):310-311, (2005). UI/OAB bladder control preparation was not associated with any side effects.

Herbal medications have previously shown effectiveness for UI and OAB without these unwanted anticholinergic side effects; however, the duration of treatment needed for these effects are two to three months. Steels et at ACJ (2002); Schauss et al, FASEB (2006). This study has shown that UI/OAB bladder control preparation reduced symptoms of UI and OAB and improved quality of life within a 2 to 4 week timeframe.

Conclusion

The results of this study indicate that UI/OAB bladder control preparation was effective in reducing symptoms of urinary incontinence and OAB, including frequency, nocturia, incontinence and urgency. Symptom relief occurred after two weeks of treatment, with the severity of symptoms reducing further at month 1. Earlier herbal combinations had shown effectiveness over a 2 to 3 month period.

The UI/OAB bladder control preparation assessed in this trial was suitable for both men and women, did not produce any anticholinergic or other major side effects and halved pad usage after one month of treatment.

This study shows that the herbal combination of *C. nurvala, E. arvense* and *L. aggregata* shows increased effectiveness in reducing symptoms of UI and OAB and improving quality of life than previous herbal combination formulations and within a shorter timeframe.

Example 2

Comparison of the Effectiveness of the Different Herbal Formulations (Formulation 3 and UI/OAB Bladder Control Preparation) for Use in the Prevention and Treatment of Urinary Incontinence and Overactive Bladder (OAB)

General

The aim of this study was to compare the efficacy of two formulations, Formula 3 (as described above in Example 4 of U.S. Pat. No. 7,378,115) and UI/OAB test preparation (presently described compositions) in treating the symptoms of urinary incontinence and OAB by analysing the results of the Incontinence Impact Questionnaire (IIQ) and the Urogenital Distress Inventory (UDI) and day and night time urinary frequency from each of the studies on the individual formulations. Formula 3 had an *E. arvense* extract standardized for silicon and flavonoid content combined with *C. nurvala* and minerals, as provided above and in Example 4 of U.S. Pat. No. 7,378,115. UI/OAB bladder control preparation uses a combination of non-standardized *E. arvense* extract combined with *C. nurvala* and *L. aggregata* and was assessed in Example 1.

Study Design

In order to directly compare the effectiveness of the two different tablet formulations, percent (%) reduction in frequency of urination and nocturia for each formulation were directly assessed and compared. In addition, bothered ratings for both questionnaires at month 1 were compared. This method of analysis was used for comparison as month 0 (baseline) values in each of the studies varied.

Results and Discussion

The results of the number (%) of people on each formula experiencing symptoms at Month 1 was assessed and compared. Comparison of the frequency of urination and nocturia indicate that UI/OAB bladder control formula was more effective in reducing the frequency of urination during the day (35% reduction at month 1 for UI/OAB formula compared to 25% reduction at month 1 for Formula 3). UI/OAB formula was also superior to Formula 3 in reducing nocturia with an 86% reduction at month 1 compared to 40% reduction at month 1 for Formula 3.

TABLE 6

| Percent Decrease in Frequency of Urination | | | |
|---|---|---|---|
| Day | | Night | |
| Formula 3 | UI/OAB test prep | Formula 3 | UI/OAB test prep |
| Month 0 vs. Month 1 | 26 | 35 | 40 | 86 |

The results of the number (%) of people bothered by their symptoms was also assessed and compared. The results from the Urinary Distress Inventory (UDI) indicate that the UI/OAB bladder control preparation had a higher effectiveness at month 1, as compared to Formula 3 (FIG. 5; Table 6).

UI/OAB test preparation showed a higher percentage reduction at month 1 for frequent urination, leakage due to feeling of urgency and activity and small amounts of leakage (drops). Results for difficulty emptying bladder have been included; however, due to the low number of participants experiencing this symptom for UI/OAB bladder control formulation, the results were not significant.

Month 1 results for UI/OAB bladder control preparation were more comparable to month 3 results for Formula 3, showing that UI/OAB bladder control preparation produces results within a much shorter timeframe.

Comparison of the Incontinence Impact Questionnaire (IIQ) also indicated that UI/OAB bladder control preparation had a faster and better response (shown by reduction in symptoms) to all the QOL questions than Formula 3 at month 1.

TABLE 7

Percent reduction in bothered rating of UDI for UI/OAB bladder control preparation and Formula 3 at month 1 and Formula 3 at month 3

| | UI/OAB BC Preparation Month 1 | Formula 3 Month 1 | Formula 3 Month 3 |
|---|---|---|---|
| Frequent Urination | 69 | 6 | 71 |
| Leakage due to urgency | 71 | 26 | 74 |
| Leakage related to activity | 65 | 33 | 68 |
| Small amounts of leakage (drops) | 73 | 28 | 66 |
| Difficulty in emptying bladder | 66 | 18 | 63 |

Conclusion

The results of this study indicate that UI/OAB bladder control preparation is safe and was not associated with major adverse reactions. It was effective in reducing symptoms of urinary incontinence and OAB, including frequency, nocturia, incontinence and urgency.

Figure 5:
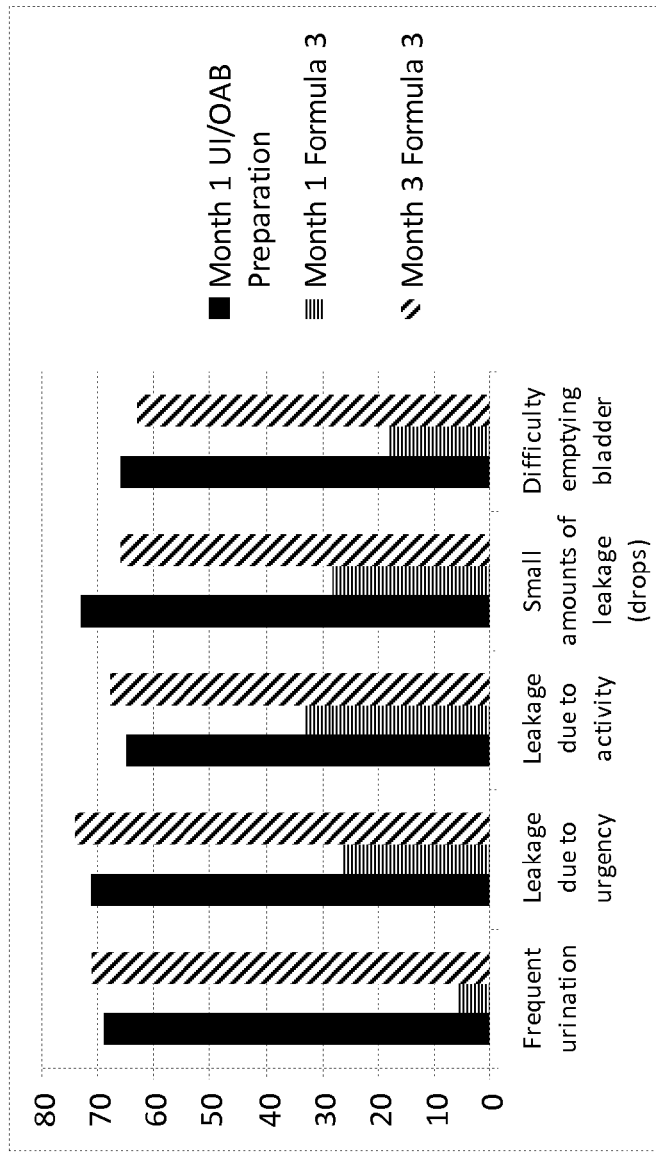
FIG. 5 is a histogram graph showing percentage (%) reduction in UDI ratings during clinical assessment in one embodiment.

As suggested by the results in Table 7 and FIG. 5, UI/OAB bladder control preparation gave symptom relief with the severity of symptoms reduction being faster and more marked than for Formula 3 at month 1 of treatment. UI/OAB gave greater reduction in urinary frequency in the day 35 versus 26% reduction) and nocturia (86 versus 40% reduction) at month 1. Results produced by UI/OAB bladder control preparation after one month of treatment were comparable, and in some instances better than those produced by Formula 3 after 3 months of treatment.

In summary, UI/OAB bladder control formula, containing *C. nurvala*, *E. arvense* and *L. aggregata* showed improved and faster effectiveness in reducing symptoms of urinary incontinence and OAB when compared to earlier herbal combinations shown to be effective in this area. This combination of *C. nurvala*, and *L. aggregata* with non-standardized *E. arvense* showed superior results over the Formula 3 containing *C. nurvala, E. arvense* standardized for silicon and flavonoids and minerals.

These two examples indicate that the composition and method described herein are effective in helping subjects control their symptoms of UI/OAB and other bladder control problems without the side effects of traditional medical treatments and provide effective prevention or treatment of the symptoms of UI/OAB in a much shorter term than the prior herbal treatments.

Example 3

Case Studies

Case 1

45 year old male with a history of bladder frequency since childhood. He was diagnosed as a child, via cystometric studies, as having a small bladder. He was not medicated.

He presented urinary frequency, every 1.5 hours; nocturia (waking for the toilet at night) every 1.5 to 2.5 hours.

If he consumed large quantities of alcohol (greater than 8 standard drinks), he would experience flooding nocturesis (bed wetting). In anticipation of nocturesis, he would lay down towels on bed when drinking.

After 2 weeks on the herb-containing natural therapeutic bladder control preparation, he noticed improvement in day and night urinary frequency. Improvements in energy throughout the day were linked with reduction in night frequency. After 4 weeks, he was experiencing periods of up to 6.5 hours in the day without the need for urination. Nocturia was an average of 1 by this stage.

He then went on holiday for 2 weeks where daily drinking of alcohol was involved. He expected the nocturesis to recur but found he had full bladder control overnight over the entire 2 weeks.

After two months on the herb-containing natural therapeutic bladder control preparation, his bladder control was in the 'normal' classification of 6-8 times daily urination and maximum of one episode of nocturia per night. He also had no nocturesis.

Case 2

73 year old woman with stress incontinence (2-7 times daily) and urinary frequency (11 times daily). She had previously tried Detrol and oral oxybutynin but could not tolerate the side effects of dry mouth and nasal passages. When presented, she was using oxybutynin patches (Oxytrol). A specialist recommended that she change patches every 3 days. She found the drying side effects still occurred but to a lesser degree, so the patches were more tolerable. The patches produced a rash for her as well so she was actively seeking an alternative.

She stopped the oxybutynin patches (after the recommended 3 day period) and then commenced on the herb-containing natural therapeutic bladder control preparation. Within two weeks, she was experiencing the same effects as the patches but without the side effects. The patient had no discernible side effects from the herb-containing natural therapeutic bladder control preparation. She has now been on the herb-containing natural therapeutic bladder control preparation for 9 weeks, has had no incontinence episodes, and has normal urinary frequency.

Case 3

63 year old male presented with interstitial cystitis that had been worsening for at least the past 5 years. He presented with penile pain (and some lower abdominal pain) that would increase in intensity the fuller his bladder, with relief on urination. As a result, he would need to urinate at least every 1.5 hours, day and night. If he went too long, the pain would increase to the point where he found it extremely difficult to walk or move. Every month, he would have an episode, usually during the night, where he would pass copious amounts of blood and some mucous from the bladder.

He would also find that every two weeks his symptom severity would increase and he would have "horrific, sharp pain all day every day" for two days. He would urinate every half hour over these two days.

He is a farmer and whilst with frequent urination he could 'manage' his condition, he was finding it increasingly difficult, for example, especially if he was in the middle of an activity such as harvesting or 'under a truck doing repairs'. Also, he was extremely fatigued due to waking in pain and needing to empty his bladder every 1.5 hours.

He had been under the care of a urologist for two years. However, drug therapy is not an option for him.

One year ago he had a bladder expansion procedure with good success. He had slight bleeding from the bladder post-operatively but had symptom relief, which lasted about three months. He had another bladder expansion procedure 6 months after the first and did not respond as well. He had much greater blood loss post-operatively and his symptoms worsened significantly. It took three months for him to recover to the point he was at prior to the procedure. He is not willing to undergo another bladder expansion procedure.

After three weeks on a double dose of the herb-containing natural therapeutic bladder control preparation (4 capsules daily), he felt an unusual sensation in the bladder and then for three or four days, when urinating, he would pass predominantly blood and mucous.

After the fourth day, his urine returned back to normal and his daytime penile pain did not reoccur. He was going to the toilet every 2.5 hours. Also, at night he could sleep for 2.5 hours before the pain would wake him for the toilet.

He continued with the double dose of the herb-containing natural therapeutic bladder control preparation and at the 2.5 month stage his overall pain is "minimal" and he can go up to 4 hours without having to get up at night for the toilet.

The pain does still recur twice weekly for half a day where he needs to urinate every hour (previously this would occur every two weeks and he would need to urinate every half hour for 2 days). He did have a slight bleed from the bladder in the middle of the night at the month 2 stage. Otherwise there has been no blood loss from the bladder since three weeks of treatment.

If all is progressing well, at 3 months his dose will be reduced to 2 capsules daily.

EQUIVALENTS

This invention has been described in terms of specific embodiments set forth in detail herein, but it should be understood that these are by way of illustration and the invention is not necessarily limited thereto. Modifications and variations will be apparent from the disclosure and may be resorted to without departing from the spirit of the invention as those of skill in the art will readily understand. Accordingly, such variations and modifications are considered to be within the purview and scope of the invention and the following claims.

What is claimed is:

1. An herb for treating or reducing the symptoms of urinary incontinence or overactive bladder comprising effective amounts of:
    (i) a *Crateva nurvala* extract preparation;
    (ii) an *Equisetum arvense* extract preparation; and
    (iii) a *Lindera aggregata* extract preparation;
    wherein the herb-containing composition is formulated as an oral dosage unit whereby the oral dosage unit is in a form selected from a tablet, capsule or caplet.

2. The herb-containing composition of claim 1, wherein the *Crateva nurvala* extract preparation is standardized to have lupeol content not less than 1.5% and tannin content not less than 2% based on the total weight of the standardized *Crateva nurvala* extract preparation.

3. The herb-containing composition of claim 1, wherein the *Equisetum arvense* extract preparation is standardized to have lupeol content not less than 1.5% and tannin content not less than 2% based on the total weight of the standardized *Equisetum arvense* extract preparation.

4. The herb-containing composition of claim 1, wherein the *Lindera aggregata* extract preparation is standardized to have lupeol content not less than 1.5% and tannin content not less than 2% based on the total weight of the standardized *Lindera aggregata* extract preparation.

5. The herb-containing composition of claim 1, wherein the *Crateva nurvala* extract preparation is present at a concentration from about 1 g to about 18 g dry weight equivalents per oral dosage unit.

6. The herb-containing composition of claim 1, wherein the *Equisetum arvense* extract preparation is present at a concentration from about 750 mg to about 12 g dry weight equivalents per oral dosage unit.

7. The herb-containing composition of claim 1, wherein the *Lindera aggregata* extract preparation is present at a concentration from about 750 mg to about 12 g dry weight equivalents per oral dosage unit.

8. The herb-containing composition of claim 1, wherein at least one of the extract is as follows:
    (i) the *Crateva nurvala* extract preparation is a bark extract preparation;
    (ii) the *Equisetum arvense* extract preparation is a stem extract preparation; and
    (iii) the *Lindera aggregata* extract preparation is a root extract preparation.

9. The herb-containing composition of claim 1, wherein the oral dosage unit is formulated as a controlled-release vehicle.

10. A pharmaceutical composition comprising the herb-containing composition of claim 1 and a pharmaceutically-acceptable carrier.

11. An herb for treating or reducing the symptoms of urinary incontinence or overactive bladder comprising effective amounts of:
    (i) a *Crateva nurvala* bark extract preparation;
    (ii) an *Equisetum arvense* stem extract preparation;
    (iii) a *Lindera aggregata* root extract preparation;
    wherein the herb-containing composition is formulated as an oral dosage unit, whereby the oral dosage unit is in a form selected from a tablet, capsule or caplet, and wherein the *Equisetum arvense* stem extract preparation and the *Lindera aggregata* root extract preparation are present at the same concentration.

12. A pharmaceutical composition comprising the herb-containing composition of claim 11 and a pharmaceutically-acceptable carrier.

\* \* \* \* \*